United States Patent
Dewal

(10) Patent No.: US 11,479,811 B2
(45) Date of Patent: Oct. 25, 2022

(54) EXPANSION MICROSCOPY COMPATIBLE AND MULTIPLEXED IN SITU HYBRIDIZATION OF FORMALIN FIXED PARAFFIN EMBEDDED TISSUE SECTIONS FOR SPATIALLY RESOLVED TRANSCRIPTOMICS

(71) Applicant: EXPANSION TECHNOLOGIES, Boston, MA (US)

(72) Inventor: Mahender Babu Dewal, Arlington, MA (US)

(73) Assignee: EXPANSION TECHNOLOGIES, Boston, MA (US)

(*) Notice: Subject to any disclaimer, the term of this patent is extended or adjusted under 35 U.S.C. 154(b) by 147 days.

(21) Appl. No.: 16/765,341

(22) PCT Filed: Nov. 20, 2018

(86) PCT No.: PCT/US2018/061931
§ 371 (c)(1),
(2) Date: May 19, 2020

(87) PCT Pub. No.: WO2019/103996
PCT Pub. Date: May 31, 2019

(65) Prior Publication Data
US 2020/0354782 A1    Nov. 12, 2020

Related U.S. Application Data

(60) Provisional application No. 62/588,940, filed on Nov. 21, 2017.

(51) Int. Cl.
*C12Q 1/6841* (2018.01)
*G01N 1/30* (2006.01)

(52) U.S. Cl.
CPC ............ *C12Q 1/6841* (2013.01); *G01N 1/30* (2013.01); *C12Q 2525/301* (2013.01); *C12Q 2527/125* (2013.01)

(58) Field of Classification Search
CPC .. C12Q 1/68; C12Q 1/6841; C12Q 2525/301; G01N 1/30; G01N 33/53; C12N 15/10
See application file for complete search history.

(56) References Cited

U.S. PATENT DOCUMENTS

| | | | |
|---|---|---|---|
| 8,911,942 B2 | 12/2014 | Mohammed et al. | |
| 10,309,879 B2 | 6/2019 | Chen et al. | |
| 2002/0110738 A1* | 8/2002 | Takizawa | H01M 10/0565 429/317 |
| 2006/0051741 A1 | 3/2006 | Tanaka et al. | |
| 2007/0141711 A1* | 6/2007 | Stephens | G01N 35/00722 436/43 |
| 2010/0260769 A1* | 10/2010 | Sass | C07K 16/2851 424/156.1 |
| 2010/0291152 A1 | 11/2010 | Shone et al. | |
| 2014/0024024 A1 | 1/2014 | Sood et al. | |
| 2015/0267251 A1 | 9/2015 | Cai et al. | |
| 2016/0116384 A1 | 4/2016 | Chen et al. | |
| 2016/0362730 A1 | 12/2016 | Alexander et al. | |
| 2017/0009278 A1 | 1/2017 | Soderberg et al. | |
| 2017/0067096 A1* | 3/2017 | Wassie | C12Q 1/6806 |
| 2017/0253918 A1 | 9/2017 | Kohman | |
| 2018/0010166 A1* | 1/2018 | Pierce | C12Q 1/6816 |
| 2018/0052081 A1 | 2/2018 | Kohman | |
| 2018/0216161 A1* | 8/2018 | Chen | C12Q 1/6855 |
| 2019/0301980 A1* | 10/2019 | Anderson | G01N 35/04 |

FOREIGN PATENT DOCUMENTS

| | | |
|---|---|---|
| EP | 1947105 | 7/2008 |
| WO | WO2016/168825 | 10/2016 |
| WO | WO2017/139501 | 8/2017 |
| WO | WO2017/143317 | 8/2017 |
| WO | WO2019/075091 | 4/2019 |

OTHER PUBLICATIONS

Chang et al., Iterative Expansion Microscopy . Nature Methods 14(6) : 593 (Year: 2017).*
Chen et al., Spatially resolved, highly multiplexed RNA profiling in single cells. Science 348: aaa6290 (Year: 2015).*
Chen et al.,Nanoscale imaging of RNA with expansion microscopy. Nature Methods 13(8) : 679 (Year: 2016).*
Chozinski et al., Expansion microscopy with conventional antibodies and fluorescent proteins. Nature Methods 13(6) :485 (Year: 2016).*
Going et al. Practical Histrological microdissection for PCR analysis J. of Pathology 179 :121 (Abstract Only) (Year: 1996).*
Ke et al., In situ sequencing for RNA analysis in preserved tissue and cells. Nature Methods 10(9) : :857 (Year: 2013).*
Ku et al.,Multiplexed and scalable super-resolution imaging of three-dimensional protein localization in size-adjustable tissues. Nature Biotechnology 34(9) : 973 (Year: 2016).*
Larsson et al., In situ genotyping individual DNA molecules by target-primed rolling-circle amplification of padlock probes. Nature Methods 1(3) :227 (Year: 2004).*
LLubeck & Cai. Single-cell systems biology by super-resolution imaging and combinatorial labeling. Nature Method 9(7) : 743 (Year: 2012).*
Lubeck et al., Single-cell in situ RNA profiling by sequential hybridization. Nature Methods 11(4) : 360-361 (Year: 2014).*
Stellwaden, Electrophoresis 19 : 1542-1547 (Year: 1998).*
Tillberg et al., Protein-retention expansion microscopy of cells and tissues labeled using standard fluorescent proteins and antibodies. Nature Biotechnology 34(9) : 987 (Year: 2016).*
Tong et al., ExM-STORM :Expansion Single Molecule Nanoscopy. bioRXiv (posted Apr. 2016) (Year: 2016).*

(Continued)

*Primary Examiner* — Ethan C Whisenant
(74) *Attorney, Agent, or Firm* — Mark S. Cohen; Pearl Cohen Zedek Latzer Baratz LLP

(57) ABSTRACT

The invention relates to imaging, such as in situ imaging by expansion microscopy, labelling, and analyzing biological samples, such as formalin fixed paraffin embedded (FFPE) cells and tissues, as well as reagents and kits for doing so.

19 Claims, 4 Drawing Sheets

(56) References Cited

OTHER PUBLICATIONS

Weibrecht et al., In situ detection of individual mRNA molecules and protein complexes or post-translational modifications using padlock probes combined with the in situ proximity ligation assay. Nature Protocols 8(2) : 355 (Year: 2013).*

Zhao et al., Nanoscale imaging of clinical specimens using pathology-optimized expansion microscopy. Nature Biotechnology 35(8) : 757 (Year: 2017).*

Atta et al., "Swelling Behaviors of Polyelectrolyte Hydrogels Containing Sulfonate Groups"; Polym. Adv. Technol., 2002, vol. 13, pp. 567-576.

Chen et al., "Expansion microscopy"; Science, Jan. 30, 2015, vol. 347(6221): pp. 543-548.

Chen et al., "Supplementary Material for Expansion Microscopy"; Science Express DOI: 10.1126/science. 1260088, Jan. 15, 2015, 18 pages.

Gao et al., "Q&A: Expansion microscopy", BMC Biology 2017 (15):50.

Le Goff et al., "Hydrogel microparticles for biosensing"; European. Polymer Journal, 2015, vol. 72, pp. 386-412.

Maruani et al., "A plug-and-play approach to antibody-based therapeutics via a chemoselective dual click strategy"; Nature Communications, 2015, 6:6645 doi: 10.1038/ncoms7645.

Okay, O.; "General Properties of Hydrogels", Hydrogel Sensors and Actuators, 2009, G. Gerlach and K.-F. Arndt (eds.), Springer Series on Chemical Sensors and Biosensors 6, Springer-Verlag Berlin Heidelberg 2009 (15 pages).

Skouri et al., "Swelling and Elastic Properties of Polyelectrolyte Gels"; Macromolecules, 1995, vol. 28, pp. 197-210.

Wahlby et al., "Sequential Immunofluorescence Staining and Image Analysis for Detection of Large Numbers of Antigens in Individual Cell Nuclei"; Cytometry, 2002, vol. 47, pp. 32-41.

International Search Report and Written Opinion dated Feb. 7, 2019 in respect of PCT Int'l Application No. PCT/US18/061931.

International Search Report and Written Opinion dated Dec. 27, 2018 in respect of PCT Int'l Application No. PCT/US18/055254.

* cited by examiner

ED
EXPANSION MICROSCOPY COMPATIBLE AND MULTIPLEXED IN SITU HYBRIDIZATION OF FORMALIN FIXED PARAFFIN EMBEDDED TISSUE SECTIONS FOR SPATIALLY RESOLVED TRANSCRIPTOMICS

CROSS-REFERENCE TO RELATED APPLICATIONS

This application is a National Phase Application of PCT International Application No. PCT/US2018/061931, International Filing Date Nov. 20, 2018, claiming the benefit of U.S. Provisional Patent Application No. 62/588,940, filed Nov. 21, 2017, which are hereby incorporated by reference.

FIELD OF THE INVENTION

The invention relates to imaging, such as in situ imaging by expansion microscopy, labelling, and analyzing biological samples, such as formalin fixed paraffin embedded (FFPE) cells and tissues, as well as reagents and kits for doing so.

BACKGROUND OF THE INVENTION

In situ transcriptional profiling of clinical formalin fixed paraffin embedded (FFPE) tissues has the potential to contribute to the development of accurate and reliable diagnoses for diseases, such as cancer. However the analysis of ribonucleic acid (RNA) within clinical samples is currently constrained by the diffraction limit of conventional microscopes which reduce the accuracy of RNA spot count quantification. Additionally, the limited number of transcripts (typically 3-4 depending on the number of available fluorescent channels) further reduces the ability to systematically map transcriptional variations across a large number of genes.

Current imaging technologies for analyzing RNA in clinical samples include RNA fluorescent in situ hybridization combined with conventional paraffin removal (e.g., Hughes et al., Anal. Methods [2014] 6:1028) and antigen retrieval, followed by widefield or confocal imaging. Techniques for transcriptional profiling of complex tissues include confocal microscopy or super-resolution microscopy of RNA in situ hybridization targets, either via RNA fluorescence in situ hybridization (FISH) (e.g., Chaumeil et al., "Combined Immunofluorescence, RNA Fluorescent In Situ Hybridization, and DNA Fluorescent In Situ Hybridization to Study Chromatin Changes, Transcriptional Activity, Nuclear Organization, and X-Chromosome Inactivation" (ch. 18, pp. 297-308) in R. Hancock (ed), *The Nucleus: Vol. 1: Nuclei and Subnuclear Components* [Humana Press 2008]), or via RNA hybridization chain reaction (HCR) (e.g., Dirks & Pierce, *Proc. Natl. Acad. Sci.* [2004] 101(43): 15275; U.S. Pat. Nos. 7,727,721, 8,124,751, and 8,507,204; Choi et al., *ACS Nano.* [2014] 8(5): 4284; Shah et al., *Development* [2016] 143:2862).

In expansion microscopy (ExM), 3-dimensional imaging with nanoscale precision is performed on cells and tissues. This is accomplished by physically expanding the biological sample using a dense polymer matrix. The first step of this process involves treating the tissue with a fluorescent protein-binding-group (typically an antibody) that selectively binds to the protein being analyzed. Next the sample is infused with a monomer solution that permeates into the tissue. Free radical polymerization of this solution creates a polymer network that is physically connected to the protein-binding-groups through customized bioconjugation chemistry. Lastly, the tissue is digested and the hydrogel (and fluorescent dyes) expands uniformly. The result is a polymer network that contains fluorescent dyes where the target proteins were located. This process has many advantages. Notably, it allows pseudo super-resolution imaging with conventional confocal microscopy because the imaging targets are no longer diffraction limited. Additionally, the tissue digestion clears the sample allowing imaging deep into thick tissues samples. (See, e.g., LeGoff et al., *Eur. Polym. J.* [2015] http://dx.doi.org/10.1016/j.eurpolymj.2015.02.022)

Critical to the success of the ExM process is the ability to physically connect the fluorescent protein-binding-groups to the polymer network. Current ExM attachment chemistry uses a trifunctional, double-stranded DNA linker to accomplish this. Because the tissue digestion enzymes are also capable of digesting the antibodies typically used as protein-binding-groups, the fluorescent dyes must be attached to the DNA and not the antibody. Also needed is the presence of a chemical group that can polymerize into the gel matrix. Current examples of ExM use a chemical arrangement in which one strand of DNA is connected to the protein-binding-group while the complementary strand possesses both the dye and the polymerizable group. Using this strategy, cells and brain tissue were successfully stained with up to 3 different protein-binding-groups, expanded, and imaged (Chen et al., *Science* 347:543 [2015]; Chen et al., "Nanoscale Imaging of RNA with Expansion Microscopy," *Nature Methods* 13:679 [2016]). However, because the number of fluorescent dyes that can be used is small (typically <6), this strategy is limited to imaging only a small number of proteins per sample. Additionally, the polymerization process dampens the fluorescence of the dyes, which are permanently connected to the gel matrix. By rearranging the location of the three chemical groups (dye, gel binding group, and protein-binding-group) on the DNA linker, previous limitations in protein imaging some previous limitations have been overcome.

However, use of DNA/antibody conjugates has also had several disadvantages. Buffers with uncommon additives are necessary in order to prevent the DNA on the antibody from binding to the nuclear DNA in the sample. Also, the presence of the DNA on the antibody reduces the extent and the rate at which it binds to the target. The result is that the current ExM processes are lengthy, and the staining is commonly dim compared to controls, making this approach laborious, time consuming, and inefficient for RNA detection due to the limited number of transcripts which can be resolved within a single specimen.

Alternatively, attempts have been made to overcome problems of ExM with respect to dim staining by utilizing an improved bioconjugation strategy or by utilizing turbo-expansion microscopy (TurboExM), which does not use DNA as a linker, and samples can be rapidly stained. TurboExM relies on antibodies, which can be directly acrylated (and hence suitable for polymerization), either before, after, or at the same time as attachment with a detectable label, but also that the detectable label will remain after the tissue digestion step, which is necessary for ExM. However, this approach is suitable for protein targets but not RNA detection.

The interrogation of RNA in clinical samples in a highly multiplexed and efficient manner remains a challenge in structural biology and medicine.

Surprisingly, it has been found that by combining serial RNA hybridization strategies with ExM, it is possible to read multiplexed RNA transcript data from FFPE clinical tissue samples. This approach allows for high speed transcriptional profiling of a large number of genes in clinical samples for diagnostic, prognostic and other purposes.

SUMMARY OF THE INVENTION

In one aspect, provided herein are methods of labeling nucleic acids and proteins together in a formalin fixed paraffin embedded (FFPE) biological tissue sample adhered on a slide, the methods comprising: (a) performing deparaffinization and antigen retrieval on the sample; (b) contacting the sample with a first gel binding moiety and a second gel binding moiety under conditions wherein the first gel binding moiety operably links to proteins in the sample and the second gel binding moiety operably links to nucleic acids in the sample; (c) contacting the sample with a solution comprising monomers of a polyelectrolyte gel; (d) by free radical polymerization, polymerizing the monomers to form the polyelectrolyte gel and covalently conjugating the first and second gel binding moieties to the polyelectrolyte gel; (e) proteolytically digesting the sample; (f) detaching the polyelectrolyte gel from the slide; (g) dialyzing the polyelectrolyte gel to expand it; (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (i) contacting the gel with the plurality of initiator DNA probes under conditions wherein the sequence complementary to the sequence from one of the nucleic acid targets of interest hybridizes to that sequence from the nucleic acid target of interest; (j) for each initiator DNA probe, providing a pair of fluorophore-labeled DNA hairpins that metastably co-exist in the absence of the initiator DNA probe; and (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe. In some embodiments, the methods further comprise, prior to step (h), embedding the expanded gel in a polyacrylamide gel matrix. In some embodiments, the methods further comprising, prior to step (b): (I) contacting the sample with one or more primary antibodies under conditions where they selectively recognize one or more target proteins of interest; and (II) contacting the sample with one or more secondary antibodies operably linked to a detectable label. In some embodiments, the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

In another aspect, provided herein are methods of labeling a formalin fixed paraffin embedded (FFPE) biological sample comprising a plurality of ribonucleic acid (RNA) targets of interest and adhered on a slide, the methods being performed under RNAse-free conditions and the methods comprising: (a) performing deparaffinization and antigen retrieval on the sample; (b) contacting the sample with a gel binding moiety under conditions wherein the gel binding moiety operably links to RNA in the sample; (c) contacting the sample with a solution comprising monomers of a polyelectrolyte gel; (d) by free radical polymerization, polymerizing the monomers to form the polyelectrolyte gel and covalently conjugating the gel binding moiety to the polyelectrolyte gel; (e) proteolytically digesting the sample; (f) detaching the polyelectrolyte gel from the slide; (g) dialyzing the polyelectrolyte gel to expand it; (h) providing a plurality of initiator deoxyribonucleic acid (DNA) probes targeting the plurality of RNA targets of interest, wherein each of the plurality of initiator DNA probes comprise (A) a sequence complementary to a sequence from one of the RNA targets of interest, and (B) a hybridization chain reaction (HCR) initiator sequence; (i) contacting the gel with the plurality of initiator DNA probes under conditions wherein the sequence complementary to the sequence from one of the RNA targets of interest hybridizes to that sequence from the RNA target of interest; (j) for each initiator DNA probe, providing a pair of fluorophore-labeled DNA hairpins that metastably co-exist in the absence of the initiator DNA probe; and (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe. In some embodiments, the methods further comprise, prior to step (h), embedding the expanded gel in a polyacrylamide gel matrix.

In another aspect, provided herein are methods of imaging nucleic acids and proteins together in a formalin fixed paraffin embedded (FFPE) biological sample adhered on a slide, the methods comprising: (a) performing deparaffinization and antigen retrieval on the sample; (b) contacting the sample with a first gel binding moiety and a second gel binding moiety under conditions wherein the first gel binding moiety operably links to proteins in the sample and the second gel binding moiety operably links to nucleic acids in the sample; (c) contacting the sample with a solution comprising monomers of a polyelectrolyte gel; (d) by free radical polymerization, polymerizing the monomers to form the polyelectrolyte gel and covalently conjugating the first and second gel binding moieties to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (i) contacting the gel with the plurality of initiator DNA probes under conditions wherein the sequence complementary to the sequence from one of the nucleic acid targets of interest hybridizes to that sequence from the nucleic acid target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (l) obtaining an image of the gel. In some embodiments, the methods further comprise, prior to step (h), embedding the expanded gel in a polyacrylamide gel matrix. In some embodiments, the methods further comprising, prior to step (b): (I) contacting the sample with one or more primary antibodies under conditions where they selectively recognize one or more target proteins of interest; and (II) contacting the sample with one or more secondary antibodies operably linked to a detectable label. In some embodiments, the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

In another aspect, provided herein are methods of imaging ribonucleic acid (RNA) in a formalin fixed paraffin embedded (FFPE) biological sample adhered on a slide, the methods being performed under RNAse-free conditions and the methods comprising: (a) performing deparaffinization and antigen retrieval on the sample; (b) contacting the sample with a gel binding moiety under conditions wherein the gel binding moiety operably links to RNA in the sample; (c) contacting the sample with a solution comprising monomers of a polyelectrolyte gel; (d) by free radical polymerization, polymerizing the monomers to form the polyelectrolyte gel and covalently conjugating the gel binding moiety to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (i) contacting the gel with the plurality of initiator DNA probes under conditions wherein the sequence complementary to the sequence from one of the RNA targets of interest hybridizes to that sequence from the RNA target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (l) obtaining an image of the gel. In some embodiments, the methods further comprise, prior to step (h), embedding the expanded gel in a polyacrylamide gel matrix.

In another aspect, provided herein are methods of imaging nucleic acids and proteins together in a formalin fixed paraffin embedded (FFPE) biological sample adhered on a slide, the methods comprising: (a) performing deparaffinization and antigen retrieval on the sample; (b) contacting the sample with a first gel binding moiety and a second gel binding moiety under conditions wherein the first gel binding moiety operably links to proteins in the sample and the second gel binding moiety operably links to nucleic acids in the sample; (c) contacting the sample with a solution comprising monomers of a polyelectrolyte gel; (d) by free radical polymerization, polymerizing the monomers to form the polyelectrolyte gel and covalently conjugating the first and second gel binding moieties to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (i) contacting the gel with the plurality of initiator DNA probes under conditions wherein the sequence complementary to the sequence from one of the nucleic acid targets of interest hybridizes to that sequence from the nucleic acid target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (l) obtaining an image of the gel; (m) treating the gel with a deoxyribonuclease to remove the initiator DNA probes and amplification polymers; and (n) repeating steps (h)-(m) one or more times for additional RNA targets of interest. In some embodiments, the methods further comprise, prior to step (h), embedding the expanded gel in a polyacrylamide gel matrix. In some embodiments, the methods further comprising, prior to step (b): (I) contacting the sample with one or more primary antibodies under conditions where they selectively recognize one or more target proteins of interest; and (II) contacting the sample with one or more secondary antibodies operably linked to a detectable label. In some embodiments, the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

In another aspect, provided herein are methods of imaging ribonucleic acid (RNA) in a formalin fixed paraffin embedded (FFPE) biological sample adhered on a slide, the methods being performed under RNAse-free conditions and the methods comprising: (a) performing deparaffinization and antigen retrieval on the sample; (b) contacting the sample with a gel binding moiety under conditions wherein the gel binding moiety operably links to RNA in the sample; (c) contacting the sample with a solution comprising monomers of a polyelectrolyte gel; (d) by free radical polymerization, polymerizing the monomers to form the polyelectrolyte gel and covalently conjugating the gel binding moiety to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (i) contacting the sample with the plurality of initiator DNA probes under conditions wherein the sequence complementary to the sequence from one of the RNA targets of interest hybridizes to that sequence from the RNA target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (l) obtaining an image of the gel; (m) treating the gel with a deoxyribonuclease to remove the initiator DNA probes and amplification polymers; and (n) repeating steps (h)-(m) one or more times for additional RNA targets of interest. In some embodiments, the methods further comprise, prior to step (h), embedding the expanded gel in a polyacrylamide gel matrix.

In another aspect, provided herein are additional methods, as well as reagents (e.g., the binding compositions, labels nucleic acid probes) and kits for use in the methods described herein.

Other features and advantages of this invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein. The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
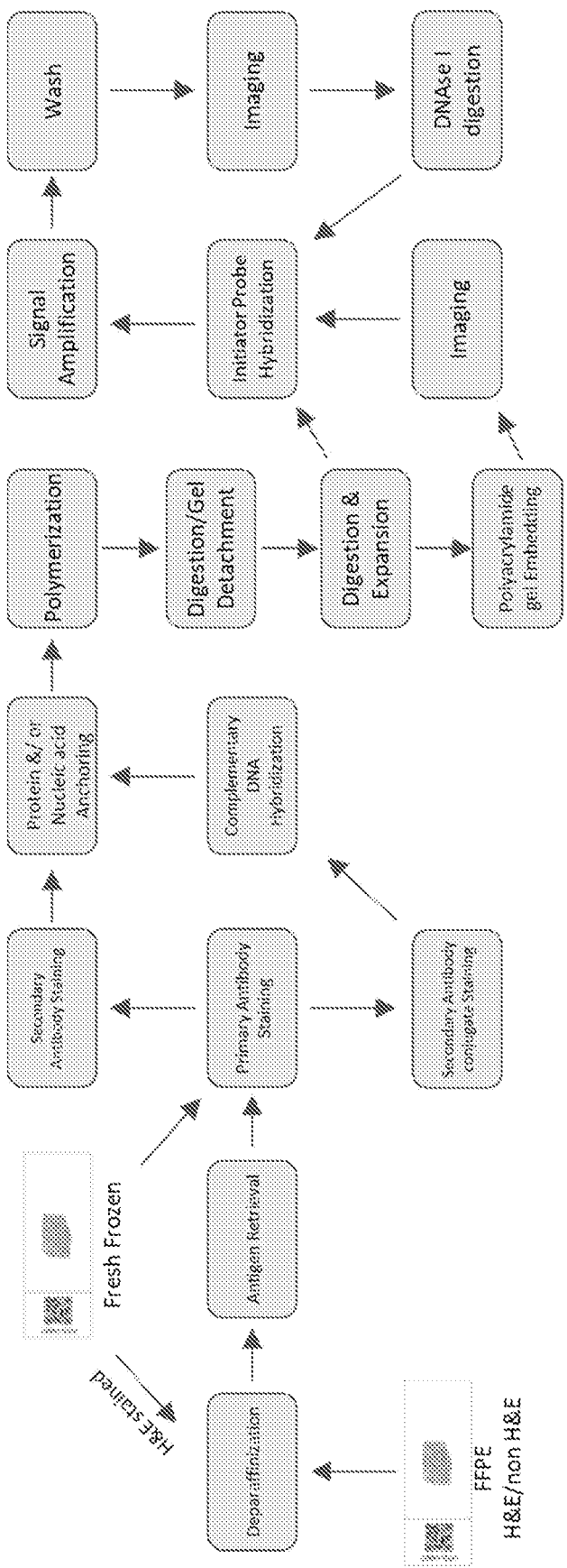
FIGS. 1A-1B. Schematic depictions of serial hybridization and removal of multiple (n-number) probes.

In aspects of this invention, the technique for expansion microscopy (ExM) is employed in order to spatially resolve multiplexed super-resolution ribonucleic acid (RNA) targets within cleared formalin fixed paraffin embedded (FFPE) tissue samples. In ExM, biological samples are permeated with a solution of water soluble small-molecule monomers which are polymerized into a swellable hydrogel that can expand upon addition of water, allowing for an enhancement in spatial resolution and specimen clearing. The tissues are then stained for RNA genes of interest, imaged, and denatured to displace the probes. The tissues can then be re-stained for new RNA genes, thereby facilitating serial labeling and readout of a large number of probes in a single sample across thick specimen regions. This, in turn, allows for effective transcriptional profiling of thousands of genes across entire complex tissues.

In ExM, 3-dimensional imaging with nanoscale precision is performed on cells and tissues. This is accomplished by physically expanding the biological sample using a dense polymer matrix.

In some embodiments, methods are provided to anchor native nucleic acids within formalin fixed paraffin embedded (FFPE) tissue samples and to perform the ExM procedure to physically expand the specimens, to employ a hybridization chain reaction (HCR) signal amplification strategy in order to obtain high signal-to-noise puncta readout, and optionally, to use DNAse I to dislocate and wash out the initiator probes and rehybridize new probes for serial hybridization.

In some embodiments, the sample is contacted with a gel binding moiety that operably links (typically covalently) to RNA in the sample. Next the sample is infused with a monomer solution that permeates into the tissue. Free radical polymerization of this solution creates a polymer network that is covalently conjugated to the gel binding moiety, (optionally also physically connected to protein-binding-groups either through a linker molecule or a customized bioconjugation chemistry). The sample is then digested and the hydrogel expands uniformly. Then, the sample is treated with an RNA-binding-group (typically a single-stranded nucleic acid, such as a deoxyribonucleic acid [DNA] primer) that selectively binds to the RNA being analyzed, and then labeled (typically fluorescently) by HCR amplification. The result is a polymer network that contains fluorescent dyes where the target RNAs are (and optionally also where target proteins were) located. This process has many advantages. Notably, it allows pseudo super resolution imaging with conventional confocal microscopy because the imaging targets are no longer diffraction limited. Additionally, the tissue digestion clears the sample allowing imaging deep into thick tissues samples.

Significant to the success of the ExM process, as used in embodiments for protein detection, has been the ability to physically connect the fluorescent protein-binding-groups to the polymer network. In one example, ExM attachment chemistry uses a trifunctional, double-stranded DNA linker to accomplish this. Because the tissue digestion enzymes are also capable of digesting the antibodies typically used as protein-binding-groups, it has been understood that fluorescent dyes must be attached to the DNA and not the antibody. Also needed is the presence of a chemical group that can polymerize into the gel matrix (e.g., a methacrylamide or dimethylacrylamide group) on the DNA. In another example, proteins and antibodies are directly linked to the polymer network using a linker molecule (e.g., Acryloyl-X (6-((acryloyl)amino)hexanoic acid succinimidyl ester)) with a methacrylamide group.

In some embodiments, the ExM process uses a chemical arrangement in which one strand of DNA (the probe) is connected to the RNA while a mismatched tail sequence of the probe DNA is hybridized to a second, complementary DNA fragment that possesses both the dye and the polymerizable group. This approach focuses on the number of dyes intended for analytical use.

Alternative bioconjugation strategies can be utilized. The locations of the three necessary chemical groups (dye, gel binding group, and RNA-binding-group) on the DNA probe and on the second, complementary DNA can be rearranged.

In other embodiments, the dye is not attached to the same DNA strand as the gel binding group. The consequence is that the final polymer matrix is physically connected to a strand of DNA with a defined sequence (and no dye). Whereas one embodiment replaces the target RNA with a dye that can be imaged, this embodiment replaces the target RNA with a DNA barcode. This barcode can be decoded in a subsequent step using multiplexed fluorescence in situ hybridization (FISH) which is not limited by the number of available fluorescent dyes. This modification in chemistry can allow the simultaneous tagging of many proteins in the same sample or tissue section because each protein can be given a unique barcode. The small number of dyes is not limiting and the maximum number of RNA targets that can be imaged is limited now by the number of available DNA primers. Additionally, because the DNA strand attached to the dye is not bound to the polymer matrix, the loss in fluorescence observed during polymerization is irrelevant because the dye-containing strand can be removed. Imaging of the barcode can be done later with FISH. In one embodiment of this approach, the DNA probe hybridized to the RNA target has a tail comprising the dye, while the second DNA sequence complementary to the tail is attached to the gel binding group. In another embodiment of this approach, the DNA probe hybridized to the RNA target has a tail comprising the gel binding group, while the second DNA sequence complementary to the tail is attached to the dye.

In one aspect, provided herein are methods of labeling nucleic acids and proteins together in a formalin fixed paraffin embedded (FFPE) biological sample adhered on a slide, the methods comprising: (a) performing deparaffinization and antigen retrieval on the sample; (b) contacting the sample with a first gel binding moiety and a second gel binding moiety under conditions wherein the first gel binding moiety operably links to proteins in the sample and the second gel binding moiety operably links to nucleic acids in the sample; (c) contacting the sample with a solution comprising monomers of a polyelectrolyte gel; (d) by free radical polymerization, polymerizing the monomers to form the polyelectrolyte gel and covalently conjugating the first and second gel binding moieties to the polyelectrolyte gel; (e) proteolytically digesting the sample; (f) detaching the polyelectrolyte gel from the slide; (g) dialyzing the polyelectrolyte gel to expand it; (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (i) contacting the gel with the plurality of initiator DNA probes under conditions wherein the sequence complementary to the sequence from one of the nucleic acid targets of interest hybridizes to that sequence from the nucleic acid target of interest; (j) for each initiator DNA probe, providing a pair of fluorophore-labeled DNA hairpins that metastably co-exist in the absence of the initiator DNA probe; and (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe. In some embodiments, the methods further comprise, prior to step (h), embedding the expanded gel in a polyacrylamide gel matrix. In some embodiments, the expanded gel is embedded in a polyacrylamide gel matrix in a borate buffer. In some embodiments, the methods further comprising, prior to step (b): (I) contacting the sample with one or more primary antibodies under conditions where they selectively recognize one or more target proteins of interest; and (II) contacting the sample with one or more secondary antibodies operably linked to a detectable label. In some embodiments, the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

In another aspect, provided herein are methods of labeling a formalin fixed paraffin embedded (FFPE) biological sample comprising a plurality of ribonucleic acid (RNA) targets of interest and adhered on a slide, the methods being performed under RNAse-free conditions and the methods comprising: (a) performing deparaffinization and antigen retrieval on the sample; (b) contacting the sample with a gel binding moiety under conditions wherein the gel binding moiety operably links to RNA in the sample; (c) contacting the sample with a solution comprising monomers of a polyelectrolyte gel; (d) by free radical polymerization, polymerizing the monomers to form the polyelectrolyte gel and covalently conjugating the gel binding moiety to the polyelectrolyte gel; (e) proteolytically digesting the sample; (f) detaching the polyelectrolyte gel from the slide; (g) dialyzing the polyelectrolyte gel to expand it; (h) providing a plurality of initiator deoxyribonucleic acid (DNA) probes targeting the plurality of RNA targets of interest, wherein each of the plurality of initiator DNA probes comprise (A) a sequence complementary to a sequence from one of the RNA targets of interest, and (B) a hybridization chain reaction (HCR) initiator sequence; (i) contacting the gel with the plurality of initiator DNA probes under conditions wherein the sequence complementary to the sequence from one of the RNA targets of interest hybridizes to that sequence from the RNA target of interest; (j) for each initiator DNA probe, providing a pair of fluorophore-labeled DNA hairpins that metastably co-exist in the absence of the initiator DNA probe; and (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe. In some embodiments, the methods further comprise, prior to step (h), embedding the expanded gel in a polyacrylamide gel matrix. In some embodiments, the expanded gel is embedded in a polyacrylamide gel matrix in a borate buffer.

In another aspect, provided herein are methods of imaging nucleic acids and proteins together in a formalin fixed paraffin embedded (FFPE) biological sample adhered on a slide, the methods comprising: (a) performing deparaffinization and antigen retrieval on the sample; (b) contacting the sample with a first gel binding moiety and a second gel binding moiety under conditions wherein the first gel binding moiety operably links to proteins in the sample and the second gel binding moiety operably links to nucleic acids in the sample; (c) contacting the sample with a solution comprising monomers of a polyelectrolyte gel; (d) by free radical polymerization, polymerizing the monomers to form the polyelectrolyte gel and covalently conjugating the first and second gel binding moieties to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (i) contacting the gel with the plurality of initiator DNA probes under conditions wherein the sequence complementary to the sequence from one of the nucleic acid targets of interest hybridizes to that sequence from the nucleic acid target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (l) obtaining an image of the gel. In some embodiments, the methods further comprise, prior to step (h), embedding the expanded gel in a polyacrylamide gel matrix. In some embodiments, the methods further comprise, prior to step (h), embedding the expanded gel in a polyacrylamide gel matrix. In some embodiments, the expanded gel is embedded in a polyacrylamide gel matrix in a borate buffer. In some embodiments, the methods further comprising, prior to step (b): (I) contacting the sample with one or more primary antibodies under conditions where they selectively recognize one or more target proteins of interest; and (II) contacting the sample with one or more secondary antibodies operably linked to a detectable label. In some embodiments, the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

In another aspect, provided herein are methods of imaging ribonucleic acid (RNA) in a formalin fixed paraffin embedded (FFPE) biological sample adhered on a slide, the methods being performed under RNAse-free conditions and the methods comprising: (a) performing deparaffinization and antigen retrieval on the sample; (b) contacting the sample with a gel binding moiety under conditions wherein the gel binding moiety operably links to RNA in the sample; (c) contacting the sample with a solution comprising monomers of a polyelectrolyte gel; (d) by free radical polymerization, polymerizing the monomers to form the polyelectrolyte gel and covalently conjugating the gel binding moiety to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (i) contacting the gel with the plurality of initiator DNA probes under conditions wherein the sequence complementary to the sequence from one of the RNA targets of interest hybridizes to that sequence from the RNA target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; and (l) obtaining an image of the gel. In some embodiments, the methods further comprise, prior to step (h), embedding the expanded gel in a polyacrylamide gel matrix. In some embodiments, the expanded gel is embedded in a polyacrylamide gel matrix in a borate buffer.

In another aspect, provided herein are methods of imaging nucleic acids and proteins together in a formalin fixed paraffin embedded (FFPE) biological sample adhered on a slide, the methods comprising: (a) performing deparaffinization and antigen retrieval on the sample; (b) contacting the sample with a first gel binding moiety and a second gel binding moiety under conditions wherein the first gel binding moiety operably links to proteins in the sample and the second gel binding moiety operably links to nucleic acids in the sample; (c) contacting the sample with a solution comprising monomers of a polyelectrolyte gel; (d) by free radical polymerization, polymerizing the monomers to form the polyelectrolyte gel and covalently conjugating the first and second gel binding moieties to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence; (i) contacting the gel with the plurality of initiator DNA probes under conditions wherein the sequence complementary to the sequence from one of the nucleic acid targets of interest hybridizes to that sequence from the nucleic acid target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (l) obtaining an image of the gel; (m) treating the gel with a deoxyribonuclease to remove the initiator DNA probes and amplification polymers; and (n) repeating steps (h)-(m) one or more times for additional RNA targets of interest. In some embodiments, the methods further comprise, prior to step (h), embedding the expanded gel in a polyacrylamide gel matrix. In some embodiments, the expanded gel is embedded in a polyacrylamide gel matrix in a borate buffer. In some embodiments, the methods further comprising, prior to step (b): (I) contacting the sample with one or more primary antibodies under conditions where they selectively recognize one or more target proteins of interest; and (II) contacting the sample with one or more secondary antibodies operably linked to a detectable label. In some embodiments, the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

In another aspect, provided herein are methods of imaging ribonucleic acid (RNA) in a formalin fixed paraffin embedded (FFPE) biological sample adhered on a slide, the methods being performed under RNAse-free conditions and the methods comprising: (a) performing deparaffinization and antigen retrieval on the sample; (b) contacting the sample with a gel binding moiety under conditions wherein the gel binding moiety operably links to RNA in the sample; (c) contacting the sample with a solution comprising monomers of a polyelectrolyte gel; (d) by free radical polymerization, polymerizing the monomers to form the polyelectrolyte gel and covalently conjugating the gel binding moiety to the polyelectrolyte gel; (e) proteolytically digesting said sample; (f) detaching the polyelectrolyte gel from the slide; (g) dialyzing the polyelectrolyte gel to expand it; (h) providing a plurality of initiator deoxyribonucleic acid (DNA) probes targeting a plurality of RNA targets of interest, wherein each of the plurality of initiator DNA probes comprise (A) a sequence complementary to a sequence from one of the RNA targets of interest, and (B) a hybridization chain reaction (HCR) initiator sequence; (i) contacting the sample with the plurality of initiator DNA probes under conditions wherein the sequence complementary to the sequence from one of the RNA targets of interest hybridizes to that sequence from the RNA target of interest; (j) for each initiator DNA probe, providing a pair of fluorophore-labeled DNA hairpins that metastably co-exist in the absence of the initiator DNA probe; (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe; (l) obtaining an image of the gel; (m) treating the gel with a deoxyribonuclease to remove the initiator DNA probes and amplification polymers; and (n) repeating steps (h)-(m) one or more times for additional RNA targets of interest. In some embodiments, the methods further comprise, prior to step (h), embedding the expanded gel in a polyacrylamide gel matrix. In some embodiments, the expanded gel is embedded in a polyacrylamide gel matrix in a borate buffer.

In another aspect, provided herein are additional methods, as well as reagents (e.g., the binding compositions, labels nucleic acid probes) and kits for use in the methods described herein.

In some embodiments, the methods described herein further comprises obtaining an image the sample or gel. In some embodiments, the image is obtained by confocal microscopy.

With respect to the above methods, compositions, or kits, in some embodiments, the RNA target of interest comprises mRNA. In some embodiments, the RNA target of interest is an mRNA target of interest and the sequence complementary to a sequence from the mRNA target of interest is at least partially complementary to an exon of said mRNA and at least partially complementary to an intron adjacent to said exon.

With respect to the above methods, an image of the sample or gel may be obtained before expanding the polyelectrolyte gel, as well as after expanding the polyelectrolyte gel.

With respect to the above methods, compositions, or kits, in some embodiments, deparaffinization comprises incubation with a hydrocarbon solvent, followed by at least two washes with decreasing concentrations of an alcohol. In some embodiments, the hydrocarbon solvent is xylene, hexane or a combination thereof. In some embodiments, the alcohol is ethanol.

With respect to the above methods, compositions, or kits, in some embodiments, the sample is rehydrated after deparaffinization and before antigen retrieval by immersing it in a buffer. In some embodiments, said buffer is selected from the group consisting of phosphate buffered saline (PBS), Tris-buffered saline (TBS), and MOPs.

With respect to the above methods, compositions, or kits, in some embodiments, antigen retrieval comprises reducing methylene bridges. In some embodiments, antigen retrieval comprises heat-induced epitope retrieval (HIER). In some embodiments, HIER comprises incubation in a HIER buffer comprising a citrate buffer, a 2-amino-2-(hydroxymethyl) propane-1,3-diol (Tris) buffer, an ethylenediaminetetraacetic acid (EDTA) buffer, a Tris-EDTA buffer, a citrate-EDTA buffer, a Tris-buffered saline (TBS), or MOPs. In other embodiments, antigen retrieval comprises proteolytic-induced epitope retrieval (PIER) or enzyme-induced antigen retrieval (EIAR). In some embodiments, PIER or EIAR comprises incubation with trypsin, proteinase K, pepsin, pronase, or protease. In still other embodiments, antigen retrieval comprises room temperature epitope retrieval (RTER), frozen section epitope retrieval, or retrieval with citraconic anhydride. In some embodiments, RTER comprises incubation with hydrochloric acid or incubation with formic acid.

With respect to the above methods, compositions, or kits, in some embodiments, the initiator probe is linked to detectable label. Examples of an initiator probe-linked detectable label include, but are not limited to, a fluorescent label or a fluorophore. Additional examples of an initiator probe-linked detectable labels include, but are not limited to, fluorescein isothiocyanate (FITC), tetramethylrhodamine (TRITC), 4',6-diamidino-2-phenylindole (DAPI), cyanine dye 5 (Cy5), Alexa 488, Alexa 514, Alexa 546, Alexa 594, and Alexa 647.

With respect to the above methods, compositions, or kits, in some embodiments, detectable labels are used (e.g., detectably-labeled DNA hairpins). Examples of detectable labels include, but are not limited to, fluorescent labels or fluorophores. Examples of fluorophores include, but are not limited to, fluorescein isothiocyanate (FITC), tetramethylrhodamine (TRITC), 4',6-diamidino-2-phenylindole (DAPI), or cyanine dye 5 (Cy5), Alexa 488, Alexa 514, Alexa 546, Alexa 594, and Alexa 647. In some embodiments, for a pair of fluorophore-labeled DNA hairpins both hairpins are labeled with the same fluorophore. In some embodiments, for a pair of fluorophore-labeled DNA hairpins each hairpin is labeled with a different fluorophore. In some embodiments, only one of the pair of fluorophore-labeled DNA hairpins is labeled with a fluorophore. Examples of fluorophores used to label DNA hairpins for HCR include, but are not limited to, fluorescein isothiocyanate (FITC), tetramethylrhodamine (TRITC), 4',6-diamidino-2-phenylindole (DAPI), or cyanine dye 5 (Cy5), Alexa 488, Alexa 514, Alexa 546, Alexa 594, and Alexa 647.

With respect to the above methods, compositions, or kits, in some embodiments, detection reagents specific for the detectable labels are provided.

In some embodiments, the methods described herein further comprise the step of: removing the initiator DNA probes unhybridized to the RNA target(s) of interest.

In some embodiments, the initiator DNA probes are preferably between 56 and 60 nucleotides in length. In some embodiments, the fluorophore-labeled DNA hairpins are preferably between 72 and 74 nucleotides in length.

With respect to the above methods, compositions, or kits, in some embodiments, the gel binding moiety is an acryloyl or methacryloyl group. In some embodiments, the gel binding moiety is Acryloyl-X (6-((acryloyl)amino)hexanoic acid succinimidyl ester). In some embodiments, the gel binding moiety comprises Nuclix:

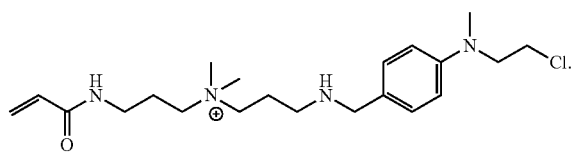 [SMILES: C=CC(=O)NCCC[N+](C)(C)CCCNCc1ccc(N(C)CCCl)cc1]

In some embodiments, the monomer solution comprises sodium acrylate, acrylamide, N—N'-methylenebisacrylamide, and N,N-dimethyl-acrylamide. In some embodiments, free radical polymerization is induced with ammonium persulfate (APS) initiator and tetramethylethylenediamine (TEMED).

With respect to the above methods, in some embodiments, dialyzing the sample or polyelectrolyte gel to expand it comprises dialyzing the sample or polyelectrolyte gel in water.

With respect to the above methods, compositions, or kits, in some embodiments, the methods further comprise performing the method on a plurality of biological samples in an array or in a microarray. In some embodiments, the array comprises a multiwell plate with each of the plurality of biological samples in a separate well of the multiwell plate. In some embodiments, the multiwell plate comprises a multiwell format of 12, 24, 48, or 96 wells. In some embodiments, said multiwell format comprises a high-throughput multiwell format.

With respect to the above methods or kits, in some embodiments, at least a portion of the method is automated.

With respect to the above methods, compositions, or kits, in some embodiments, the biological sample is derived from a multicellular organism. In some embodiments, the multicellular organism is a vertebrate. In some embodiments, the vertebrate is a mammal or a bird. In some embodiments, the mammal is a human. Alternatively, in some embodiments, the mammal is a non-human mammal. In some embodiments, the biological sample is a brain, heart, lung, gastrointestinal, circulatory, kidney, urogenital, pancreatic, gall bladder, muscle, breast, prostrate, bladder, ear, eye, glandular, or bone sample. In some embodiments, the biological sample comprises serial sections from a single organism, such as a human, and the methods described herein further comprise repeating the method on the serial sections in an array comprising a multiwell plate where each of the serial sections is ordered in a separate well of the plate. Examples of serial sections may include cross-sections or sagittal sections, such as those of an organ, a portion of an organ, a whole organism, or a portion of an organism. An organism includes an embryo. A biological sample may be fresh, frozen, previously mounted, or fresh-frozen.

In some embodiments, the methods described herein further comprise obtaining images of the plurality of serial sections and constructing a three-dimensional model from those images.

With respect to the above methods, compositions, and kits, in some embodiments, the initiator DNA probe has a dissociation constant ($K_D$) less than about $1\times10^{-5}$ M, less than about $1\times10^{-6}$ M, or less than about $1\times10^{-7}$ M. With respect to the above methods, compositions, and kits, in some embodiments, the hairpin molecules have a dissociation constant ($K_D$) less than about $1\times10^{-5}$ M, less than about $1\times10^{-6}$ M, or less than about $1\times10^{-7}$ M.

In some embodiments, the methods further comprise the step of removing the gel binding moieties unconjugated to the polyelectrolyte gel after free radical polymerization.

With respect to methods, in some embodiments, target biomolecules, such as proteins, are detected with antibodies, which include primary and secondary antibodies, or antigen-binding fragments. In some embodiments, the antibodies may be monoclonal or polyclonal antibodies. In some embodiments, the antigen-binding fragments may be derived from polyclonal or monoclonal antibodies. In some embodiments, the antigen-binding fragment is selected from the group consisting of a Fab, a Fab', a (Fab')$_2$, a F(ab')2, a Fv, a single chain antibody (SCA), and a scFv-Fc. In some embodiments, the affinity of the antigen-binding site for the expansion target biomolecule is a high affinity with an affinity constant ($K_a$) greater than $10^4$ $M^{-1}$ or it is between $10^5$-$10^{11}$ $M^{-1}$. A specific binding composition may have a dissociation constant ($K_D$) less than about $1\times10^{-5}$ M, less than about $1\times10^{-6}$ M, or less than about $1\times10^{-7}$ M.

In some embodiments, where preparation of a microarray is concerned, the method also comprises capture element synthesis, preparation of a solid support surface, immobilization of capture elements onto the solid support (e.g., via a robotic arrayer), binding of the target molecule to the immobilized capture elements, and detection and quantification of the target/capture element complex. In some embodiments, at least some part of the method is automated.

Nucleic Acids

As used herein, the terms "polynucleotide" and "nucleic acid molecule" are used interchangeably to refer to polymeric forms of nucleotides of any length, which may have any three-dimensional structure, and may perform any function, known or unknown. The polynucleotides may contain deoxyribonucleotides (DNA), ribonucleotides (RNA), and/or their analogs, including, but not limited to, single-, double-stranded and triple helical molecules, a gene or gene fragment, exons, introns, messenger RNA (mRNA), transfer RNA (tRNA), ribosomal RNA (rRNA), small interfering RNA (siRNA), micro RNA (miRNA), ribozymes, antisense molecules, complementary DNA (cDNA), genomic DNA (gDNA), recombinant polynucleotides, branched polynucleotides, aptamers, plasmids, vectors, isolated DNA sequences, isolated RNA sequences, nucleic acid probes, peptide nucleic acids (PNA), and primers. A nucleic acid molecule may also comprise modified nucleic acid molecules (e.g., comprising modified bases, sugars, and/or internucleotide linkers).

"Nucleic materials" and "materials from the nucleus" include the nuclear envelope and the contents of the nucleus, including genomic DNA (gDNA) or plasmid DNA. The "non-nucleic acid contents of the nucleus" include the components of the nuclear envelope and any other proteins or other substances of the nucleus that are not nucleic acids.

"Nucleic acids" include deoxyribonucleic acids (DNA) and ribonucleic acids (RNA) of various types, including genomic DNA (gDNA) and messenger RNA (mRNA) and derivatives thereof, such as modified DNA or RNA, including peptide nucleic acids (PNA). "Peptide nucleic acid" (PNA) is a polynucleotide analog in which the sugar-phosphate backbone is replaced by amide bonds. "Genetic material" comprises genomic DNA (gDNA), which is one type of DNA and encodes genetic information, or genetic RNA.

As used herein, a "genetic modification" refers to an addition, deletion or disruption to a cell's normal nucleotides. Art recognized methods include viral mediated gene transfer, liposome mediated transfer, transformation, transfection and transduction. As used herein, a "genetic mutation" is a genetic alteration and is a type of "genetic modification."

As used herein, a "polymorphism" or "genetic polymorphism" is a genetic variation and includes, but is not limited to, a single nucleotide polymorphism (SNP). As used herein, a "genotype" is the genetic composition of an organism, and a "phenotype" is the physical appearance or characteristics of an organism.

A "peptide" is a compound of two or more subunit amino acids, amino acid analogs, or peptidomimetics. The subunits may be linked by peptide bonds or by other bonds (e.g., as esters, ethers, and the like). An "amino acid" refers to either natural and/or unnatural or synthetic amino acids, including glycine and both D or L optical isomers, and amino acid analogs and peptidomimetics. "Amino acids" also includes imino acids. An "oligopeptide" refers to a short peptide chain of three or more amino acids. If the peptide chain is long (e.g., greater than about 10 amino acids), the peptide is a "polypeptide" or a "protein." While the term "protein" encompasses the term "polypeptide," a "polypeptide" may be a less than full-length protein.

As used herein, "expression" refers to the process by which polynucleotides are transcribed into mRNA and/or translated into peptides, polypeptides, or proteins. If the polynucleotide is derived from genomic DNA, expression may, but is not required to, include splicing of the mRNA transcribed from genomic DNA, capping of the 5' end of the mRNA, polyadenylation of the 3' end of the mRNA, or other processing modifications or events.

In some embodiments of the present invention, the ribonucleic acid (RNA) target of interest is a messenger RNA (mRNA).

RNA, including mRNA, is known in the art as being highly susceptible to degradation upon exposure to one or more RNAses. RNAses are present in a wide range of locations, including water, many reagents, laboratory equipment and surfaces, skin, mucous membranes, and elsewhere. It is known in the art that working with RNA generally requires preparing an RNAse-free environment and materials, as well as taking precautions to avoid introducing RNAses into an RNAse-free environment.

RNAse-free precautions are known in the art. These include, but are not limited to, cleaning surfaces with an RNAse cleaning product (e.g., RNASEZAP™ [Ambion] and other commercially available products or 0.5% sodium dodecyl sulfate [SDS] followed by 3% $H_2O_2$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor); and wearing clean gloves (while avoiding contaminated surfaces) and a clean lab coat. Some solutions (but not Tris-based solutions) can be treated with 0.5 ml DEPC/L, followed by incubation for 2 hours at 37° C., and autoclaving, preferably for at least 45 minutes. Water may be treated with 0.1% v/v DEPC for at least 2 hours at 37° C., then autoclaved. Additional techniques may be useful for procedures in which the RNA is isolated from the sample (e.g., use of TRIZOL™ [Invitrogen] reagents).

RNAses in a biological sample of interest may be inhibited either by rinsing in RNAse-free water and snap freezing the tissue, e.g., in liquid nitrogen, for use at a later date. Alternatively, the biological sample may be stored in ethanol or in an RNAse inhibitor-containing solution at −80° C.

A nucleic acid may have a sequence of at least 65% complementarity; at least 75% complementarity; at least 85% complementarity; at least 95% complementarity; at least 97% complementarity; or at least 99% complementarity to a target or other sequence of interest.

With respect to nucleic acids, "specificity" refers to identity or complementarity as a function of competition or recognition/binding, respectively. "Specificity" of recognition or binding may be affected by the conditions under which the recognition or binding takes place (e.g., pH, temperature, salt concentration, and other factors known in the art) to effect "hybridization" of one nucleic acid domain to another (see, e.g., Wetmur, "DNA Probes: Applications of the Principles of Nucleic Acid Hybridization," *Critical Reviews in Biochemistry and Molecular Biology* 26(3/4): 227-259 (1991)). It is understood that a practitioner may vary conditions without undue experimentation. For example, the practitioner may calculate the melting temperature of a DNA complex, an RNA complex, or a DNA/RNA hybrid complex and adjust conditions accordingly.

"Conservatively modified variants" of sequences may also be envisioned. With respect to particular nucleic acid sequences, conservatively modified variants refers to those nucleic acids which encode identical or essentially identical amino acid sequences, or where the nucleic acid does not encode an amino acid sequence, to essentially identical sequences. Specifically, degenerate codon substitutions can be achieved by generating sequences in which the third position of one or more selected (or all) codons is substituted with mixed base and/or deoxyinosine or other modified residues. Alternatively, one or more amino acids may be substituted with an amino acid having a similar structure, activity, charge, or other property. Conservative substitution tables providing functionally similar amino acids are well-known in the art (see, e.g., *Proc. Natl. Acad. Sci. USA* 89: 10915-10919 (1992)).

As used herein, "expression" refers to the process by which polynucleotides are transcribed into mRNA and/or translated into peptides, polypeptides, or proteins. If the polynucleotide is derived from genomic DNA, expression may include, but is not required to include, splicing of the mRNA transcribed from the genomic DNA, capping of the 5' end of the mRNA, polyadenylation of the 3' end of the mRNA, or other processing modifications or events.

Where an RNA target of interest is specifically an mRNA in the process of being transcribed or newly transcribed (but prior to the step of intron-splicing during post-transcriptional processing), such as when a practitioner is interested in changes in levels of transcription (e.g., in response to a particular stimulus) in an organism, the initiator DNA probes can be constructed to bridge an exon-intron boundary in the unprocessed mRNA sequence. For example, by using a probe that hybridizes partially to an exon of the mRNA target and partially to an intron adjacent to the exon, such that the probe domain overlaps the exon-intron boundary (i.e., the probe domain hybridizes to an exon sequences adjacent to the exon-intron boundary and intron sequences adjacent to the exon sequences at the exon-intron boundary).

Antibodies and Antigens

As used herein, the term "antibody" encompasses the structure that constitutes the natural biological form of an antibody. In most mammals, including humans, and mice, this form is a tetramer and consists of two identical pairs of two immunoglobulin chains, each pair having one light and one heavy chain, each light chain comprising immunoglobulin domains $V_L$ and $C_L$, and each heavy chain comprising immunoglobulin domains $V_H$, Cγ1, Cγ2, and Cγ3. In each pair, the light and heavy chain variable regions ($V_L$ and $V_H$) are together responsible for binding to an antigen, and the constant regions ($C_L$, Cγ1, Cγ2, and Cγ3, particularly Cγ2, and Cγ3) are responsible for antibody effector functions. In some mammals, for example in camels and llamas, full-length antibodies may consist of only two heavy chains, each heavy chain comprising immunoglobulin domains $V_H$, Cγ2, and Cγ3. By "immunoglobulin (Ig)" herein is meant a protein consisting of one or more polypeptides substantially encoded by immunoglobulin genes. Immunoglobulins include but are not limited to antibodies. Immunoglobulins may have a number of structural forms, including but not limited to full-length antibodies, antibody fragments, and individual immunoglobulin domains including but not limited to $V_H$, C$\gamma$1, C$\gamma$2, C$\gamma$3, $V_L$, and $C_L$.

Depending on the amino acid sequence of the constant domain of their heavy chains, intact antibodies can be assigned to different "classes." There are five-major classes (isotypes) of intact antibodies: IgA, IgD, IgE, IgG, and IgM, and several of these may be further divided into "subclasses," e.g., IgG1, IgG2, IgG3, IgG4, IgA, and IgA2. The heavy-chain constant domains that correspond to the different classes of antibodies are called alpha, delta, epsilon, gamma, and mu, respectively. The subunit structures and three-dimensional configurations of different classes of immunoglobulins are well known to one skilled in the art. While some antibodies are monomeric, most are multimers. As is well-known in the art, the subunits of most multimeric antibodies are linked to each other via disulfide bonds. For example, human IgG is comprised of two light chains and two heavy chains, with the two heavy chains typically linked by two disulfide bonds in the hinge region and with each light chain linked to a different heavy chain via a disulfide bond.

An "antibody" (Ab) is a protein that binds specifically to a particular substance, known as an "antigen" (Ag) (see below). An "antibody" or "antigen-binding fragment" is an immunoglobulin that binds a specific "epitope." The term encompasses polyclonal, monoclonal, and chimeric antibodies (e.g., multispecific antibodies). In nature, antibodies are generally produced by lymphocytes in response to immune challenge, such as by infection or immunization. An "antibody combining site" is that structural portion of an antibody molecule comprised of heavy and light chain variable and hypervariable regions that specifically binds antigen.

The terms "antibody" or "antigen-binding fragment" respectively refer to intact molecules as well as functional fragments thereof, such as Fab, a scFv-Fc bivalent molecule, F(ab')$_2$, and Fv that are capable of specifically interacting with a desired target. In some embodiments, the antigen-binding fragments comprise:

(1) Fab, the fragment which contains a monovalent antigen-binding fragment of an antibody molecule, which can be produced by digestion of whole antibody with the enzyme papain to yield an intact light chain and a portion of one heavy chain;

(2) Fab', the fragment of an antibody molecule that can be obtained by treating whole antibody with pepsin, followed by reduction, to yield an intact light chain and a portion of the heavy chain; two Fab' fragments are obtained per antibody molecule;

(3) (Fab')$_2$, the fragment of the antibody that can be obtained by treating whole antibody with the enzyme pepsin without subsequent reduction; F(ab')2 is a dimer of two Fab' fragments held together by two disulfide bonds;

(4) Fv, a genetically engineered fragment containing the variable region of the light chain and the variable region of the heavy chain expressed as two chains;

(5) Single chain antibody ("SCA"), a genetically engineered molecule containing the variable region of the light chain and the variable region of the heavy chain, linked by a suitable polypeptide linker as a genetically fused single chain molecule; and (6) scFv-Fc, is produced by fusing single-chain Fv (scFv) with a hinge region from an immunoglobulin (Ig) such as an IgG, and Fc regions.

In some embodiments, an antibody provided herein is a monoclonal antibody. In some embodiments, the antigen-binding fragment provided herein is a single chain Fv (scFv), a diabody, a tandem scFv, a scFv-Fc bivalent molecule, an Fab, Fab', Fv, F(ab')$_2$ or an antigen binding scaffold (e.g., affibody, monobody, anticalin, DARPin, Knottin, etc.).

An "antigen" (Ag) is any substance that reacts specifically with antibodies or T lymphocytes (T cells). An "antigen-binding site" is the part of an immunoglobulin molecule that specifically binds an antigen. Additionally, an antigen-binding site includes any such site on any antigen-binding molecule, including, but not limited to an MHC molecule or T cell receptor, but it can also include any substance against which an antibody or antigen-binding fragment has been raised, including artificially manufactured antigens and/or artificially manufactured antibodies or antigen-binding fragments.

The term "antigenic material" covers any substance that will elicit an innate or adaptive immune response. As used herein, "a portion of antigenic material" covers any antigenic material or fragment thereof, which is capable of eliciting an innate or adaptive immune response, even if the fragment is an incomplete representation or subset of the antigenic material as a whole. It can include the minimal antigen sequence required to elicit a specific immune response.

An "epitope" or "antigenic determinant" is a structure, usually made up of, but not limited to, a short peptide sequence or oligosaccharide, that is specifically recognized or specifically bound by a component of the immune system. It is the site on an antigen recognized by an antibody.

An antibody or antigen-binding fragment to a specific "expansion target biomolecule" specifically interacts with at least some component of that "expansion target biomolecule."

An "immunogen" is a substance capable of eliciting an immune response. Each immunoglobulin molecule can potentially bind a variety of antibodies directed at its unique features, or "idiotype," which is comprised of a series of "idiotopes." An "idiotope" is a single antigenic determinant on a variable region of an antibody or T cell receptor. It is the set of idiotopes on an antibody which comprise the idiotype that makes that antibody unique. The "dominant idiotype" is the idiotype found on the major fraction of antibodies generated in response to an antigen.

As used herein, the terms "binds" or "binding" or grammatical equivalents, refer to compositions, directly or indirectly, having affinity for each other. "Specific binding" is where the binding is selective between two molecules. A particular example of specific binding is that which occurs between an antibody and an antigen. Typically, specific binding can be distinguished from non-specific when the dissociation constant ($K_D$) is less than about $1\times10^{-5}$ M or less than about $1\times10^{-6}$ M or $1\times10^{-7}$ M. Specific binding can be detected, for example, by ELISA, immunoprecipitation, coprecipitation, with or without chemical crosslinking, two-hybrid assays and the like. Appropriate controls can be used to distinguish between "specific" and "non-specific" binding. "Affinity" is defined as the strength of the binding interaction of two molecules, such as an antigen and its antibody, which is defined for antibodies and other molecules with more than one binding site as the strength of binding of the ligand at one specified binding site. Although the noncovalent attachment of a ligand to antibody is typically not as strong as a covalent attachment, "high affinity" is for a ligand that binds to an antibody or other molecule having an affinity constant ($K_a$) of greater than $10^4$ $M^{-1}$, typically $10^5$-$10^{11}$ $M^{-1}$; as determined by inhibition ELISA or an equivalent affinity determined by comparable techniques, such as Scatchard plots or using $K_d$/dissociation constant, which is the reciprocal of the $K_a$, etc.

In one embodiment, the antibody, antigen-binding fragment, or affinity tag binds its target with a $K_D$ of 0.1 nM-10 mM. In one embodiment, the antibody, antigen-binding fragment, or affinity tag binds its target with a $K_D$ of 0.1 nM-1 mM. In one embodiment, the antibody, antigen-binding fragment, or affinity tag binds its target with a $K_D$ within the 0.1 nM range. In one embodiment, the antibody, antigen-binding fragment, or affinity tag binds its target with a $K_D$ of 0.1-2 nM. In another embodiment, the antibody, antigen-binding fragment, or affinity tag binds its target with a $K_D$ of 0.1-1 nM. In another embodiment, the antibody, antigen-binding fragment, or affinity tag binds its target with a $K_D$ of 0.05-1 nM. In another embodiment, the antibody, antigen-binding fragment, or affinity tag binds its target with a $K_D$ of 0.1-0.5 nM. In another embodiment, the antibody, antigen-binding fragment, or affinity tag its target with a $K_D$ of 0.1-0.2 nM. In some embodiments, the antibody, antigen-binding fragment, or affinity tag bind its target directly. In some embodiments, the antibody, antigen-binding fragment, or affinity tag bind its target indirectly, for example, the antibody, antigen-binding fragment, or affinity tag is a secondary antibody that binds to an antibody bound to the target. "Specificity" refers to the ability of an antibody to discriminate between antigenic determinants. It also refers to the precise determinants recognized by a particular receptor or antibody. "Specificity" may be affected by the conditions under which the discrimination or recognition takes place (e.g., pH, temperature, salt concentration, and other factors known in the art).

A "peptide" is a compound of two or more subunit amino acids, amino acid analogs, or peptidomimetics. The subunits may be linked by peptide bonds or by other bonds (e.g., as esters, ethers, and the like). While the term "protein" encompasses the term "polypeptide," a "polypeptide" may be less than a full-length protein. However, the terms "polypeptide" and "protein" are used herein interchangeably and refer to any polymer of amino acids (dipeptide or greater) linked through peptide bods or modified peptide bonds. Thus, the terms "polypeptide" and "protein" include oligopeptides, protein fragments, fusion proteins, and the like. It should be appreciate that the terms "polypeptide" and "protein" can include moieties such as lipoproteins and glycoproteins, except where the context dictates otherwise.

A "tag peptide sequence" is a short peptide or polypeptide chain of 3 or more amino acids, which is attached to an antibody or other protein or moiety of interest. In some embodiments, a polypeptide, protein, or chimeric protein comprises a tag polypeptide sequence, which is used for purification, detection, labeling or some other function, such as by specific binding to an antibody. The antibody may be in solution or bound to a surface. The tag peptide sequence should not interfere with the function of the rest of the polypeptide, protein, or chimeric protein. Examples of tag proteins are well-known to those of ordinary skill in the art.

Probes and Labels

The word "label" as used herein refers to a compound or composition which is conjugated or fused directly or indirectly to a reagent such as a nucleic acid probe or an antibody and facilitates detection of the reagent to which it is conjugated or fused. The label may itself be detectable (e.g., radioisotope labels or fluorescent labels) or, in the case of an enzymatic label, may catalyze chemical alteration of a substrate compound or composition, which is detectable.

As used herein, the term "probe" refers to synthetic or biologically produced nucleic acids that are engineered to contain specific nucleotide sequences which hybridize under stringent conditions to target nucleic acid sequences. Conditions, such as pH, temperature, salt concentration, and other factors known in the art, may be varied to effect "hybridization" of one nucleic acid domain to another (see, e.g., Wetmur, "DNA Probes: Applications of the Principles of Nucleic Acid Hybridization," *Critical Reviews in Biochemistry and Molecular Biology* 26(3/4): 227-259 (1991)).

As used herein, a "labeled probe," "antibody operably linked to a label," "antibody operably linked to a detectable label," "antigen-binding fragment operably linked to a label," antigen-binding fragment operably linked to a detectable label," "nucleic acid probe operably linked to a detectable label," or "nucleic acid strand operably linked to a detectable label" refer to a probe which is prepared with a marker moiety, "label" or "detectable label" for detection. The marker moiety should be linked in a place and manner so as not to interfere with, significantly/substantially decrease or inhibit, the binding or affinity of the probe to the target. For example, with respect to an antibody (or antigen-binding protein) operably linked to a label, the label should be attached to the antibody (or antigen-binding fragment) in such a manner as to prevent the label from inhibiting binding of the antibody (or antigen-binding fragment) to its expansion target biomolecule. With respect to an antibody, the marker moiety is preferably attached to a constant region of the antibody, preferably to a Cγ2 or a Cγ3 region of a heavy chain. With respect to an antigen-binding fragment, the marker moiety is preferably attached to a constant region of the antigen-binding fragment. Alternatively, the label and/or the polyelectrolyte gel binding moiety is preferably operably linked at the location of one or more disulfide linkages with the antibody. With respect to a nucleic acid, the marker moiety is attached at either the 5' end, the 3' end, internally, or in any possible combination thereof. The preferred marker moiety is an identifying label, preferably a detectable label. In some embodiments, the detectable label is a fluorophore. In some embodiments, one probe may be attached to multiple marker moieties. In some embodiments, multiple types of probes are used, each type having a different marker moiety. The labeled probe may also be comprised of a plurality of different nucleic acid sequences and/or antibodies (or antigen-binding fragments) each labeled with one or more marker moieties. Each of the marker moieties may be the same or different. It may be beneficial to label the different probes (e.g., nucleic acid sequences, antibodies or antigen-binding fragments) each with a different marker moiety. This can be accomplished by having a single distinguishable moiety on each probe. For example, probe A may be attached to moiety X and probe B may be attached to moiety Y. Alternatively, probe A may be attached to moieties X and Y while probe B may be attached to moiety Z and W. As another alternative, probe A may be attached to moieties X and Y while probe B may be attached to moieties Y and Z. All the probes "A" and "B" described above would be distinguishable and uniquely labeled.

In one embodiment, ExM attachment chemistry uses a trifunctional, double-stranded DNA linker to accomplish this. Because the tissue digestion enzymes are also capable of digesting the antibodies typically used as protein-binding-groups, the fluorescent dyes must be attached to the DNA and not the antibody. Also needed is the presence of a chemical group that can polymerize into the gel matrix (shown here as a methacrylamide group) on the DNA. Examples of ExM use the chemical arrangement where one strand of DNA is connected to the protein-binding-group while the complementary strand possesses both the dye and the polymerizable group. Using this strategy, cells and brain tissue were successfully stained with up to 3 different protein-binding-groups, expanded, and imaged. However, because the number of fluorescent dyes that can be used is small (typically <6), this strategy is limited to imaging only a small number of proteins per sample. Additionally, the polymerization process dampens the fluorescence of the dyes which are permanently connected to the gel matrix. These problems can be overcome by utilizing an improved bioconjugation strategy.

By rearranging the location of the three necessary chemical groups (dye, gel binding group, and protein-binding-group) on the DNA linker, the previous limitations in protein imaging can be overcome. In this example the dye is no longer attached to the same DNA strand as the gel binding group. The consequence is that the final polymer matrix is physically connected to a stand of DNA with a defined sequence (and no dye). This strategy replaces the target protein with a DNA barcode. This barcode can be decoded in a subsequent step using multiplexed fluorescence in situ hybridization (FISH) which is not limited by the number of available fluorescent dyes. This modification in chemistry can allow the simultaneous tagging of many proteins in the same sample because each protein can be given a unique barcode. The small number of dyes is no longer limiting and the maximum number of proteins that can be imaged is limited now by the number of available protein-binding-groups. Additionally, because the DNA strand attached to the dye is not bound to the polymer matrix, the loss in fluorescence observed during polymerization is irrelevant because the dye-containing strand can be removed. Imaging of the barcode can be done later with FISH.

"Acrylates" or "polyacrylates" are a family of polymers made from acrylate monomers, which are esters having vinyl groups. Acrylate monomers include, but are not limited to acrylamide, N-sioproylacrulamide, dimethylacrylamide, acrylic acid, methacrylic acid, hydroxyl ethyl acrylamide, or oligo(ethylene glycol) methyl ether methacrylate, which can polymerize. For example, free radical polymerization of an acrylate monomer solution comprising sodium acrylate, acrylamide, N—N'-methylenebisacrylamide, and N,N-dimethyl-acrylamide can be induced by the addition of ammonium persulfate (APS) initiator and tetramethylethylenediamine (TEMED).

In some embodiments, the antibody or antigen-binding fragment can be acrylated directly, making it suitable for polymerization. This process can be performed either before, after, or simultaneously with attachment of the detectable label (e.g., a fluorophore). The most staightforward way to acrylate antibodies is to use a reagent which can react with the many amino groups present on its surface such as the commercially available SE, 6-((acryloyl)amino) hexanoic acid, succinimidyl ester (Acryoyl-X, ThermoFisher A20770). Once the polymerizable group is presented on the surface of the antibody, free radical polymerization in its presence will result with it being attached to the polymer gel.

Direct acrylation of the antibody or antigen-binding fragment yields a "polyelectrolyte gel binding moiety" operably linked to the antibody or antigen-binding fragment. In some embodiments, the polyelectrolyte gel binding moiety is a acrylamide, methacrylamide, acrylate, or methacrylate group. For example, the reagent is SE, 6-((acryloyl)amino) hexanoic acid, succinimidyl ester (Acryoyl-X, ThermoFisher A20770).

During free radical polymerization of the acrylate monomers (above), the "polyelectrolyte gel binding moiety" is covalently conjugated to the polyelectrolyte gel, thereby indirectly attaching the labeled antibody or antigen-binding fragment to the resulting polyelectrolyte gel. The "polyelectrolyte gel binding moiety" should be linked to the antibody or antigen-binding fragment in a place and manner so as not to interfere with, significantly/substantially decrease or inhibit, the binding or affinity of the probe to the target and also so as not to interfere with, significantly/substantially decrease or inhibit, the detection of the marker moiety. For example, with respect to an antibody (or antigen-binding protein) operably linked to a polyelectrolyte gel binding moiety, the polyelectrolyte gel binding moiety should be attached to the antibody (or antigen-binding fragment) in such a manner as to prevent the polyelectrolyte gel binding moiety from inhibiting binding of the antibody (or antigen-binding fragment) to its expansion target biomolecule and should also be attached to the antibody (or antigen-binding fragment) in such a manner as to prevent the polyelectrolyte gel binding moiety from inhibiting detection of the label. With respect to an antibody, polyelectrolyte gel binding moiety is preferably attached to a constant region of the antibody, preferably to a Cγ2 or a Cγ3 region of a heavy chain. With respect to an antigen-binding fragment, the polyelectrolyte gel binding moiety is preferably attached to a constant region of the antigen-binding fragment. In some embodiments, the modified antibody comprises an antibody modified with a fluorophore operably linked to a constant region on one heavy chain and a polyelectrolyte gel binding moiety operably linked to a constant region on the other heavy chain.

In some embodiments, pyridazinediones (PD), such as a dibromopyridazinedione (diBrPD), which contain both the acrylate group and the dye, can be inserted into one or more of the disulfide linkage(s) within the antibody. (See, e.g., Maruani et al., *Nature Commun.* 6:6645 [2015] [DOI: 10/1038/ncomms7645].) With this approach, the number and location of modification sites are controlled, the solubility of the antibody undergoes little or no alteration, and the reagents maintain the structural stability of the disulfide bond.

Samples

"Biological sample" includes sample of organs, tissues, cells, blood, serum, plasma, fluid, or other materials obtained from a biological organism. It also includes a biological organism, a cell, virus, or other replicative entity. Also included are solid cultures (including bacterial or tissue cultures). Also included are solid sample, including, but not limited non-biological solids containing a biological organism, cell, virus, or other replicative entity; organs; tissues; cells; or sections (e.g., sagittal sections, cross-sections, and the like), washings, homogenizations, sonications, and similar treatments of biological samples. A biological sample may be obtained directly from a biological organism (e.g., a human or non-human animal, a plant, a fungus, a yeast, a protist, a bacterium or algae), it may be from a culture, or it may initially be attached to a non-biological solid. A biological sample may include a cancerous or noncancerous tumor or other growth, including a noncancerous aberrant growth.

A "physiological condition" of a biological organism may be normal or abnormal. The physiological condition may result from the genetic make-up of the organism (including, but not limited to, the expression of various proteins), from environmental factors (including, but not limited to, the ingestion of drugs, poisons, food, and beverages and the exposure of an organism to toxic or non-toxic substances), from disease (both infectious or non-infectious), from an injury, from a metabolic disorder, from pregnancy or nursing, and from a wide range of other circumstances, including genetic diseases, syndromes, and polymorphisms with respect to the genotype and/or phenotype of the organism, organ, tumor, tissue, or cell.

By "tissue sample" is meant a collection of similar cells obtained from a tissue of a subject or patient, preferably containing nucleated cells with chromosomal material. The four main human tissues are (1) epithelium; (2) the connective tissues, including blood vessels, bone and cartilage; (3) muscle tissue; and (4) nerve tissue. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; cells from any time in gestation or development of the subject. The tissue sample may also be primary or cultured cells or cell lines. The tissue sample may contain compounds which are not naturally intermixed with the tissue in nature such as preservatives, anticoagulants, buffers, fixatives, nutrients, antibiotics, or the like.

For the purposes herein a "tissue section" is meant a single part or piece of a tissue sample, e.g., a thin slice of tissue or cells cut from a tissue or a sample thereof. It is understood that multiple sections of tissue samples may be taken and subjected to analysis. Types of sections include sagittal sections and cross-sections and may be individual or serial.

Alternatively, "whole mounts" may be studied. "Whole mounts" include, but are not limited to, an organ or an organism.

As used herein, "cell line" refers to a permanently established cell culture that will proliferate given appropriate fresh medium and space. In some embodiments, a cell line can be cultured and expanded to form a layer of cells, such as an adherent layer of cells, over the bottom of a plate or over the bottom of a well, such as a well of a multiwell plate.

The term "subject" refers to an organism, including a mammal (including a human) in need of therapy for, or susceptible to, a condition or its sequelae. The subject may include dogs, cats, pigs, cows, sheep, goats, horses, rats, and mice and humans. The term "subject" does not exclude an individual that is normal in all respects.

"Vertebrates" include fish, reptiles, amphibians, birds (avians), and mammals. "Mammals" include, but are not limited to, murines, simians, humans, farm animals, sport animals, and pets. Mammals may be egg-laying, or they may be marsupials or placentals. "Birds" include, but are not limited to, farm animals, sport animals, and pets.

Paraffin Removal from FFPE Tissue Sections

There are several methods for paraffin removal from FFPE tissue sections. Methods include, but are not limited to, those involving incubation with a hydrocarbon solvent, such as xylene or hexane, followed by two or more washes with decreasing concentrations of an alcohol, such as ethanol. In one protocol, the tissue section is dipped 10 times into 3 mL xylene (Sigma-Aldrich Cat. 534056) or hexane (Sigma-Aldrich Cat. 139386), then immersed for times between 0-1320 minutes (preferably at least 5-10 minutes), followed by dipping 10 times into 3 mL ethanol, followed by air drying for 30 minutes (see Hughes et al., *Anal. Methods* (2014) 6:1028-1035). In another protocol, the tissue section is vortexed in 1200 microliters xylene for 30 sec, then centrifuged at full speed for 5 minutes at room temperature, followed by removal of supernatant, then two rounds of vortexing in 1200 microliters ethanol and centrifugation at full speed for 5 minutes, followed by incubation at 37° C. for 10-15 minutes, tissue lysis (Lysis Solution T, Sigma-Aldrich), digestion with 20 microliters Proteinase K at 55° C. overnight and with 20 microliters RNAse A at room temperature for 20 minutes (Sigma-Aldrich, *FFPE Tissue*). The cells may optionally be lysed, and DNA or RNA may be extracted (Id.). Alternatively, a protocol may be used in which a slide with the tissue section of interest is incubated in 4 separate aliquots of xylene for 2 minutes each, followed by incubation in 2 separate aliquots of absolute ethanol for 1 minute each, incubation in an aliquot of 95% ethanol for 30 sectioned, incubation in an aliquot of 70% ethanol for 45 seconds, and washing with water for 1 minute (Galati, Histo-Scientific Research Lab.; http://www.histosearch-.com/histonet/Mar99/Deparaffinizationprotocol.html). Another is to incubate the slide at room temperature for 60 minutes or draining in a heated dry oven at 55-60° C. for 20 minutes, then to immerse the slide in xylene for 10 minutes and repeat 1-2 times with fresh aliquots of xylene, followed by a series of immersions in ethanol (100% for 2 minutes; 95% for 1 minute; 70% for 1 minute; 50% for 1 minute; 30% for 1 minute), an immersion in 0.85% naCl solution for 2 minutes, and an immersion in 1× phosphate buffered saline (PBS) for 2 minutes (Folio ARRay of Discovery, *Deparaffinization Protocols: Tissue Arrays and Single Tissue Slides*). Another is to incubate the slide in a rack and to perform the following washes: xylene twice for 3 minutes/each; xylene: 100% ethanol (1:1) for 3 minutes; 100% ethanol twice for 3 minutes/each; 95% ethanol for 3 minutes; 70% ethanol for 3 minutes; 50% ethanol for 3 minutes; rinsing in cold tap water (Abcam, *IHC Deparaffinization Protocol*).

The tissue may be rehydrated in a buffer, such as PBS, TBS or MOPs.

Antigen Retrieval

The fixation and processing steps used in the preparation of tissues often result in the loss of antigen/epitope immunoreactivity, such as due to the formation of methylene bridges. Various approaches are available to antigen retrieval. Additional variations include time, temperature, pH, and other factors. Examples include, but are not limited to, the following:

Heat-induced Epitope Retrieval (HIER): Generally, the tissue sample is incubated in a HIER buffer (e.g., a citrate buffer, a 2-amino-2-(hydroxymethyl)propane-1,3-diol (Tris) buffer, an ethylenediaminetetraacetic acid (EDTA) buffer, a Tris-EDTA buffer, a citrate-EDTA buffer, a Tris-buffered saline (TBS)) in a pressure cooker (e.g., 1-5 minutes at 120° C.) or in a microwave or a water-heat bath for 5-40 minutes (or 10-20 minutes in a microwave or 20-40 minutes in a water-heat bath) at 90-100° C. (or 90-98° C. or 92-95° C.) (IHC World, http://www.ihcworld.com/epitope_retrieval.htm; Abcam, *IHC Antigen Retrieval Protocol: Heat induced epitope retrieval and enzymatic retrieval*; Bio-Rad Labs., Inc., *Antigen Retrieval Techniques for Use with Formalin-Fixed Paraffin-Embedded Tissues*; Novus Biologicals, https://www.novusbio.com/support/support-by-application/antigen-retrieval/protocol.html, 2017; R&D Systems, haps://www.rndsystems.com/resourees/protocols/antigen-retrieval-methods, 2017; PeproTech, www.peprotech.com; Myers, *Overview of Heat-Induced Epitope Retrieval (HIER) Techniques and* Devices, IHC World, http://www.ihcworld.com/_protocols/epitope_retrieval/overview.htm; IHC World, *Citrate Buffer Antigen*

Retrieval Protocol, http://www.ihcworld.com/_protocols/epitope_retrieval/citrate_buffer.htm; IHC World, *Citrate EDTA Antigen Retrieval Protocol*, http://www.ihcworld.com/protocols/epitope_retrieval/citrate_edta.htm; IHC World, *EDTA Buffer Antigen Retrieval Protocol*, http://www.ihcworld.com/_protocols/epitope_retrieval/edta.htm; IHC World, *Tris-EDTA Buffer Antigen Retrieval Protocol*, http://www.ihcworld.com/_protocols/epitope_retrieval/tris_edta.htm; IHC World, *Tris Buffered Saline (TBS) Antigen Retrieval Protocol*, http://www.ihcworld.com/_protocols/epitope_retrieval/tbs.htm; IHC World, *Tris Buffer Antigen Retrieval Protocol*, http://www.ihcworld.com/_protocols/epitope_retrieval/tris.htm). Alternatively, a commercially available device or kit may be used.

Proteolytic-induced Epitope Retrieval (PIER) or Enzyme-Induced Antigen Retrieval (EIAR): Generally, the tissue sample is treated with an enzyme (e.g., trypsin, proteinase K, pepsin, pronase, or protease), according to the manufacturer's protocol (e.g., incubation in a buffer at 37° C. for 10-20 minutes) (IHC World, http://www.ihcworld.com/epitope_retrieval.htm; Abcam, *IHC Antigen Retrieval Protocol: Heat induced epitope retrieval and enzymatic retrieval*; Bio-Rad Labs., Inc., *Antigen Retrieval Techniques for Use with Formalin-Fixed Paraffin-Embedded Tissues*; R&D Systems, https://www.rndsystems.com/resources/protocols/antigen-retrieval-methods, 2017; PeproTech, www.peprotech.com; IHC World, *Proteinase K Antigen Retrieval Protocol*, http://www.ihcworld.com/_protocols/epitope_retrieval/proteinase-k.htm; IHC World, *Trypsin Antigen Retrieval Protocol*, http://www.ihcworld.com/_protocols/epitope_retrieval/trypsin.htm; IHC World, *Pepsin Antigen Retrieval Protocol*, http://www.ihcworld.com/_protocols/epitope_retrieval/pepsin.htm; IHC World, *Pronase Antigen Retrieval Protocol*, http://www.ihcworld.com/_protocols/epitope_retrieval/pronase.htm; IHC World, *Protease Antigen Retrieval Protocol*, http://www.ihcworld.com/_protocols/epitope_retrieval/protease.htm). Commercially available materials may be used.

Room Temperature Epitope Retrieval (RTER): Generally, the tissue sample is treated with an acid (e.g., hydrochloric acid (pH 1) or formic acid (pH 2)) at room temperature (e.g., for 10-20 minutes) (IHC World, *Hydrochloric Acid (HCl) Antigen Retrieval Protocol*, http://www.ihcworld.com/_protocols/epitope_retrieval/hcl.htm; IHC World, *Formic Acid Antigen Retrieval Protocol*, http://www.ihcworld.com/_protocols/epitope_retrieval/formic_acid.htm).

Frozen Section Epitope Retrieval: Generally, these methods are primarily used for non-paraffin-fixed sections. Aldehyde-fixed cryostat tissue sections or cultured cells may be rinsed in buffer (e.g., PBS), incubated in 1% SDS at room temperature for 5 minutes, and rinsed again in buffer (IHC World, *Antigen Retrieval Method for Cryostat Frozen Sections*, http://www.ihcworld.com/_protocols/epitope_retrieval/frozen_section_ar.htm). Alternatively, frozen sections can be fixed in paraformaldehyde, immersed overnight in buffer (e.g., sodium citrate), boiled, incubated in cold sucrose, frozen, and then mounted (IHC World, *Antigen Retrieval Method for Frozen Sections*, http://www.ihcworld.com/_protocols/epitope_retrieval/en_bloc.htm).

Antigen Retrieval Method for Free Floating Sections, Slide-mounted Cryostat Sections and Paraffin-Embedded Slide-mounted Sections: Generally, this method involves incubation (e.g., 30 minutes) of sections in a 10-50 mM sodium citrate solution (pH 8.5-9.0) preheated to and maintained at 80° C., followed by incubation (e.g., 30 minutes) in 0.3-3% nonfat dry milk (IHC World, *Antigen Retrieval Method for Free Floating Sections*, http://www.ihcworld.com/_protocols/epitope_retrieval/free_floating_sections.htm).

Universal Antigen Retrieval Method with Citraconic Anhydride Buffer: Generally, this method involves deparaffinization, followed by incubation in 0.05% citraconic anhydride buffer (pH 7.4) in a steamer or water bath (e.g., at 95-100° C.) for 20-40 minutes Staining Protocols for FFPE Tissue Sections Various approaches are available with respect to staining for FFPE tissue sections, as discussed above. Additionally, there are the following in more detail:

Immunofluorescence: Following deparaffinization, rehydration, and antigen retrieval, the tissue sections are rinsed in buffer (e.g., PBS), then incubated with a primary antibody. The tissue sections are rinsed and blocked (e.g., with a milk solution, blocking buffer or other blocking solution), and then incubated with a target specific primary antibody/antibodies and fluorophore-conjugated secondary antibody/antibodies according to the manufacturer's instructions, and washed further.

Fluorescently labeled Streptavidin/Biotin Staining: Following deparaffinization, rehydration, and optional antigen retrieval, the tissue sections are washed in buffer (e.g., PBS-TWEEN 20®, TBS-TWEEN 20®) and optionally incubated with Triton X 100 (e.g., 2% in 1×PBS) to enhance penetration. (TWEEN 20® is polyoxyethylene (20) sorbitan monolaurate or polysorbate 20 (Sigma-Aldrich P9416).) Tissue sections may be optionally incubated with Fc receptor block to reduce non-specific binding of antibody on Fc receptors. The slides are washed and blocked with a protein block for 10 minutes. The tissue sections are incubated with avidin, washed, and then incubated with biotin and washed again. The tissue sections are then incubated with the primary antibody (e.g., 30 minutes-2 hours at room temperature or overnight at 4° C.). The slides are washed and blocked with an appropriate blocking agent for the system. The tissue sections are incubated the corresponding biotinylated secondary antibody (e.g., for 30 minutes or according to the manufacturer's instructions). Tissue sections are washed and then counterstained (e.g., with hematoxyline), then washed further and rinsed with ethanol and xylene (e.g., 95% ethanol twice for 3 minutes/each; 100% ethanol twice for 3 minutes/each; and xylene twice for 5 minutes/each) before mounting and/or imaging. (https://www.thermofisher.com/us/en/home/life-science/antibodies/biotin-binding-protein-conjugates.html).

Cross-Linking Groups for Protein Conjugation

Cross-linking groups are categorized based on on their chemical reactivities and other properties (see Chemistry of Crosslinking, Thermo Fisher Scientific, https://www.thermofisher.com/us/en/home/life-science/protein-biology/protein-biology-learning-center/protein-biology-resource-library/pierce-protein-methods/chemistry-crosslinking.html). Cross-linking groups for protein conjugation include, but are not limited to, carboxyl-to-amine reactive groups (e.g., carbodiimide, EDC/EDAC, DCC, N-hydroxysuccinimide [NHS], sulfo-N-hydroxysuccinimide [sulfo-NHS], amine-biotin reagents), amine-reactive groups (e.g., NHS ester, sulfo-NHS ester, sulfotetrafluorophenyl-STP, imidoester, pentafluorophenyl ester, hydroxymethyl phosphine), sulfhydryl-reactive groups (e.g., maleimide, haloacetyle [bromo-, iodo-], pyridyldisulfide, thiosulfonate, vinylsulfone), aldehyde-reactive groups (i.e., oxidized sugars/carbonyls; e.g., hydrazide, aldoxyamine), photoreactive groups (i.e., nonselective/random insertion; e.g., diazirine, aryl azide), chemoselective ligation groups (e.g., Staudinger reagent pairs), and hydroxyl (nonaqueous)-reactive groups (e.g., isocyanate). Typically, cross-linking groups are selected based on factors including chemical specificity, spacer arm length, water-solubility, cell membrane permeability, and/or presence of spontaneously reactive or photoreactive groups. They may be homobifunctional (i.e., having identical reactive groups at each end of a spacer arm [e.g., disuccinimidyl suberate (DSS)]) or heterobifunctional (i.e., having different reactive groups at each end of a spacer arm [e.g., sulfosuccinimidyl-4-(N-maleimidomethyl)cyclohexane-1-carboxylate (sulfo-SMCC)]).

Carbodiimides, including N-hydroxysuccinimide (NHS) and sulfo-N-hydroxysuccinimide (sulfo-NHS), are zero-length crosslinkers resulting in direct conjugation of carboxylates (—COOH) to primary amines (—$NH_2$) without becoming part of the final crosslinking amide bond between the target molecules. Sulfo-NHS is a water soluble analog of NHS.

NHS-esters are reactive groups formed by activation of carboxylate molecules. Frequently, they react with primary amines in mildly alkaline conditions (pH 7.2-8.5), resulting in stable amide bonds and releasing N-hydroxysuccinimide, which is removed, e.g., by dialysis or desalting. Sulfo-NHS esters contain a sulfonate (—$SO_3$) group on the N-hydroxysuccinimide ring. Their hydrophilicity inhibits their permeation of cell membranes and allows them to be used for cell surface applications.

Labeling biomolecules can be performed using activated esters, such as N-hydroxysuccinimide (NHS-) esters and other activated esters (including, but not limited to, sulfo-NHS, sulfotetrafluorophenyl-STP, imidoesters). These reactive compounds can be used for the modification of primary amine groups (—$NH_2$). Modifications can include fluorescent labels, fluorescence quenchers, and other reporter groups. Some embodiments include the attachment of an alkyne group or azido group. Activated esters can be used to modify proteins and peptides, as well as amino-oligonucleotides, amino-modified DNA, and amino-containing sugars. With respect to peptides and proteins, these groups are found at the N-terminus of each polypeptide chain or in the side-chain of lysine (Lys, K) amino acid residues. Because they are usually positively charged at physiological pH, peptide or protein configuration at physiological pH would typically place them on the outside surface of the tertiary structure, and their nucleophilic character would make them targets for conjugation.

Solvents for labeling can include, but are not limited to, water, dimethyl sulfoxide (DMSO), or dimethyl formamide (DMF). Non-sulfonated NHS-esters may need to be dissolved in a water-miscible organic solvent (e.g., DMSO, DMF) prior to addition to a reaction mixture, while sulfo-NHS esters are more water soluble. Preferably, reactions buffers, such as phosphate-buffered saline (PBS) are used that do not contain primary amines, while buffers with primary amines (e.g., Tris, glycine) can be used as quenching buffers.

The dibenzocyclooctyne group (DBCO; azadibenzocyclooctyne [ADIBO]; dibenzoazacyclooctyne [DIBAC]) is a cycloalkyne that is thermally stable and has a high specific reactivity toward azide groups through strain-romoted click chemistry reaction (Cu(I)-free Strain-Promoted Alkyne-Azide Click Chemistry [SPAAC]) in the absence of a catalyst (e.g., copper) or reducing agents (e.g., DTT) (See Prim et al., ADIBO-Based "Click" Chemistry for Diagnostic Peptide Micro-Array Fabrication: Physicochemical and Assay Characteristics, *Molecules* [2013] 18: 9833-9849.) Ligation occurs quickly and can yield stable triazoles. At physiological pH, the DBCO group does not react with amines or hydroxyls. Dibenzocyclooctyne-N-hydroxysuccinimide ester (DBCO-NHS ester) has a 6-carbon spacer arm, which holds the DBCO moiety close to the tagged molecule, and a terminal carboxylic acid activated as NHS ester, which can react with free amine groups to form a stable amide bond. It interacts with primary amines (N-terminus or lysine side chain) or with aminosilane-coated surfaces. DBCO can be used to label oligomers and other nucleotides at the 5' end.

DBCO-containing modification reagents include, but are not limited to, dibenzylcyclooctyne acids (e.g., dibenzylcyclooctyne acid [DBCO acid], DBCO-lc-acid, dibenzylcycloocctyne —C6-acid); dibenzylcyclooctyne amines (e.g., dibenzylcyclooctyne amine [DBCO amine]); dibenzylcyclooctyne-N-hydroxysuccinimide esters (dibenzylcyclooctyne-N-hydroxysuccinimide ester [DBCO-NHS-ester]; dibenzylcyclooctyne-sulfo-N-hydroxysuccinimide ester [DBCO-sulfo-NHS-ester]; DBCO-lc-NIH ester; dibenzylcyclooctyne-C6-NHS ester [DBCO-C6-NHS ester]; sulfo-dibenzylcyclooctyne-NHS-ester sodium salt [sulfo-DBCO-NHS-ester sodium salt]; dibenzylcyclooctyne-polyethylene glycol4-N-hydroxysuccinimide ester [DBCO-PEG4-NHS ester]; dibenzylcyclooctyne-PEG4-NHS ester; dibenzylcyclooctyne-S—S—NHS ester [DBCO—S—S—NHS ester]); dibenzylcyclooctyne melimides (e.g., dibenzylcyclooctyne-maleimide [DBCO-maleimide]); and dibenzylcyclooctyne-polyethylene glycol-4-maleimides (dibenzylcyclooctyne-polyethylene glycol-4-maleimide [DBCO-PEG4-maleimide]).

Detection Methods

In various aspects, provided herein are methods of detecting or locating a target in a biological sample or tissue section. Targets are detected by contacting a biological sample or tissue section with a target detection reagent, e.g., a single-stranded nucleic acid or a fragment thereof, and a labeling reagent. The presence or absence of targets are detected by the presence or absence of the labeling reagent, and the location of the labeling reagent indicates where the target biomolecules were located. In some instances, the biological sample or tissue section is contacted with the target detection reagent and the labeling reagent concurrently e.g., the detection reagent is a primary antibody and the labeling reagent is a fluorescent dye both of which are conjugated to a single nucleic acid strand. Alternatively, the biological sample or tissue section is contacted with the target detection reagent and the labeling reagent sequentially, e.g., the detection reagent is a primary antibody and the labeling reagent includes a secondary antibody. For example, the biological sample or tissue section is incubated with the detection reagent, in some cases together with the labeling reagent, under conditions that allow a complex between the detection reagent (and labeling reagent) and target to form. After complex formation the biological sample or tissue section is optionally washed one or more times to remove unbound detection reagent (and labeling reagent). When the biological sample or tissue section is further contacted with a labeling reagent that specifically binds the detection reagent that is bound to the target, the biological sample or tissue section can optionally be washed one or more times to remove unbound labeling reagent. The presence or absence of the target, and if present its location, in the biological sample or tissue section is then determined by detecting the labeling reagent.

Imaging technologies for transcriptional profiling of expanded complex tissues include, but are not limited to, confocal microscopy or super-resolution microscopy of RNA in situ hybridization targets, e.g., via ExM in combination with RNA fluorescence in situ hybridization (FISH) and RNA hybridization chain reaction (HCR), as described above.

The methods described herein provide for the detection of multiple targets in a sample.

Multiple targets are identified by contacting the biological sample or tissue section with additional detection reagents followed by additional labeling reagent specific for the additional detection reagents using the methods described above. For example, each target is associated with an initiator probe comprising a single-stranded nucleic acid (e.g., DNA) with a barcode or sequence specific for that target RNA of interest (e.g., an mRNA). The initiator probes optionally comprise a detectable label. To detect multiple targets simultaneously, a plurality of unique initiator probes, each recognizing either a corresponding unique domain of one or more RNA targets of interest or a unique RNA target of interest. The plurality of initiator probes can be added sequentially (with removal of the previous initiator probe prior to addition of the next one) or simultaneously. Alternatively, a different unique initiator probes can be added to each distinct well in an array on a multiwell format plate or to each spot on a micro-array.

HCR is conducted with first and second nucleic acid hairpin molecules (e.g., single-stranded DNA) at least one of which has a detectable label. In some cases, sets or subsets of labeled hairpin molecules are prepared with distinct labels, e.g., fluorophores that are distinguished by their emission spectra, e.g., one that emits in the green spectra and one that emits in the red spectra. The pairs (sets) of labeled hairpin molecules can then be added simultaneously to a biological sample to detect multiple targets at once. Alternatively, sets or subsets of labeled hairpin molecules are prepared with the same label. Each set of the labeled hairpin molecules can then be added sequentially to detect a specific target, with each set of labeled hairpin molecules removed from the biological sample prior to adding the next set of labeled hairpin molecules to detect multiple targets sequentially.

The detection moiety, i.e., detectable label, is a substance used to facilitate identification and/or quantitation of a target. Detection moieties are directly observed or measured or indirectly observed or measured. Detection moieties include, but are not limited to, radiolabels that can be measured with radiation-counting devices; pigments, dyes or other chromogens that can be visually observed or measured with a spectrophotometer; spin labels that can be measured with a spin label analyzer; and fluorescent moieties, where the output signal is generated by the excitation of a suitable molecular adduct and that can be visualized by excitation with light that is absorbed by the dye or can be measured with standard fluorometers or imaging systems, for example. The detection moiety can be a luminescent substance such as a phosphor or fluorogen; a bioluminescent substance; a chemiluminescent substance, where the output signal is generated by chemical modification of the signal compound; a metal-containing substance; or an enzyme, where there occurs an enzyme-dependent secondary generation of signal, such as the formation of a colored product from a colorless substrate. The detection moiety may also take the form of a chemical or biochemical, or an inert particle, including but not limited to colloidal gold, microspheres, quantum dots, or inorganic crystals such as nanocrystals or phosphors. The term detection moiety or detectable label can also refer to a "tag" or hapten that can bind selectively to a labeled molecule such that the labeled molecule, when added subsequently, is used to generate a detectable signal. For instance, one can use biotin, iminobiotin or desthiobiotin as a tag and then use an avidin or streptavidin fluorophore. Similarly, the tag can be a hapten or antigen (e.g., digoxigenin), and an enzymatically, fluorescently, or radioactively labeled antibody can be used to bind to the tag. Numerous labels are known by those of skill in the art and include, but are not limited to, particles, fluorescent dyes, haptens, enzymes and their chromogenic, fluorogenic, and chemiluminescent substrates, and other.

A fluorophore is a chemical moiety that exhibits an absorption maximum beyond 280 nm, and when covalently attached in a labeling reagent retains its spectral properties. Fluorophores include, without limitation; a pyrene, an anthracene, a naphthalene, an acridine, a stilbene, an indole or benzindole, an oxazole or benzoxazole, a thiazole or benzothiazole, a 4-amino-7-nitrobenz-2-oxa-1,3-diazole (NBD), a cyanine, a carbocyanine, a carbostyryl, a porphyrin, a salicylate, an anthranilate, an azulene, a perylene, a pyridine, a quinoline, a borapolyazaindacene, a xanthene, an oxazine or a benzoxazine, a carbazine, a phenalenone, a coumarin, a benzofuran and benzphenalenone and derivatives thereof. As used herein, oxazines include resorufins, aminooxazinones, diaminooxazines, and their benzo-substituted analogs.

When the fluorophore is a xanthene, the fluorophore may be a fluorescein, a rhodol, or a rhodamine. As used herein, fluorescein includes benzo- or dibenzofluoresceins, seminaphthofluoresceins, or naphthofluoresceins. Similarly, as used herein rhodol includes seminaphthorhodafluors. Alternatively, the fluorophore is a xanthene that is bound via a linkage that is a single covalent bond at the 9-position of the xanthene. Preferred xanthenes include derivatives of 3H-xanthen-6-ol-3-one attached at the 9-position, derivatives of 6-amino-3H-xanthen-3-one attached at the 9-position, or derivatives of 6-amino-3H-xanthen-3-imine attached at the 9-position. Fluorophores include xanthene (rhodol, rhodamine, fluorescein and derivatives thereof) coumarin, cyanine, pyrene, oxazine and borapolyazaindacene. In addition, the fluorophore can be sulfonated xanthenes, fluorinated xanthenes, sulfonated coumarins, fluorinated coumarins and sulfonated cyanines. The choice of the fluorophore in the labeling reagent will determine the absorption and fluorescence emission properties of the labeling reagent. Physical properties of a fluorophore label include spectral characteristics (absorption, emission and stokes shift), fluorescence intensity, lifetime, polarization and photo-bleaching rate all of which can be used to distinguish one fluorophore from another.

Typically the fluorophore contains one or more aromatic or heteroaromatic rings, that are optionally substituted one or more times by a variety of substituents, including without limitation, halogen, nitro, cyano, alkyl, perfluoroalkyl, alkoxy, alkenyl, alkynyl, cycloalkyl, arylalkyl, acyl, aryl or heteroaryl ring system, benzo, or other substituents typically present on fluorophores known in the art.

Preferably the detection moiety is a fluorescent dye. Fluorescent dyes include, for example, Fluorescein, Rhodamine, Texas Red, Cy2, Cy3, Cy5, Cy0, Cy0.5, Cy1, Cy1.5, Cy3.5, Cy7, VECTOR Red, ELF™ (Enzyme-Labeled Fluorescence), FluorX, Calcein, Calcein-AM, CRYPTOFLUOR™'S, Orange (42 kDa), Tangerine (35 kDa), Gold (31 kDa), Red (42 kDa), Crimson (40 kDa), BHMP, BHDMAP, Br-Oregon, Lucifer Yellow, Alexa dye family, N-(6-(7-nitrobenz-2-oxa-1,3-diazol-4-yl)amino)caproyl) (NBD), BODIPY™, boron dipyrromethene difluoride, Oregon Green, MITOTRACKER™ Red, DiOC7 (3), DiIC18, Phycoerythrin, Phycobiliproteins BPE (240 kDa) RPE (240 kDa) CPC (264 kDa) APC (104 kDa), Spectrum Blue, Spectrum Aqua, Spectrum Green, Spectrum Gold, Spectrum Orange, Spectrum Red, NADH, NADPH, FAD, Infra-Red (IR) Dyes, Cyclic GDP-Ribose (cGDPR), Calcofluor White, Tyrosine and Tryptophan.

Many fluorophores can also function as chromophores.

In addition to fluorophores, enzymes also find use as detectable moieties. Enzymes are desirable detectable moieties because amplification of the detectable signal can be obtained resulting in increased assay sensitivity. The enzyme itself does not produce a detectable response but functions to break down a substrate when it is contacted by an appropriate substrate such that the converted substrate produces a fluorescent, colorimetric or luminescent signal. Enzymes amplify the detectable signal because one enzyme on a labeling reagent can result in multiple substrates being converted to a detectable signal. This is advantageous where there is a low quantity of target present in the sample or tissue section or a fluorophore does not exist that will give comparable or stronger signal than the enzyme. However, fluorophores are most preferred because they do not require additional assay steps and thus reduce the overall time required to complete an assay. The enzyme substrate is selected to yield the preferred measurable product, e.g. colorimetric, fluorescent or chemiluminescence. Such substrates are extensively used in the art.

A preferred colorimetric or fluorogenic substrate and enzyme combination uses oxidoreductases such as horseradish peroxidase and a substrate such as 3,3'-diaminobenzidine (DAB) and 3-amino-9-ethylcarbazol-e (AEC), which yield a distinguishing color (brown and red, respectively). Other colorimetric oxidoreductase substrates that yield detectable products include, but are not limited to: 2,2-azino-bis(3-ethylbenzothiaz-oline-6-sulfonic acid) (ABTS), o-phenylenediamine (OPD), 3,3',5,5'-tetramethylbenzidine (TMB), o-dianisidine, 5-amino salicylic acid, 4-chloro-1-naphthol. Fluorogenic substrates include, but are not limited to, homovanillic acid or 4-hydroxy-3-methoxyphenylacetic acid, reduced phenoxazines and reduced benzothiazines, including Amplexe Red reagent and its variants and reduced dihydroxanthenes, including dihydrofluoresceins and dihydrorhodamines including dihydrorhodamine 123. Peroxidase substrates that are tyramides represent a unique class of peroxidase substrates in that they can be intrinsically detectable before action of the enzyme but are "fixed in place" by the action of a peroxidase in the process described as tyramide signal amplification (TSA). These substrates are extensively utilized to label targets in samples or tissue sections that are cells, tissues, arrays, or microarrays for their subsequent detection by microscopy, flow cytometry, optical scanning and fluorometry.

Additional colorimetric (and in some cases fluorogenic) substrates and enzyme combination use a phosphatase enzyme such as an acid phosphatase, an alkaline phosphatase or a recombinant version of such a phosphatase in combination with a colorimetric substrate such as 5-bromo-6-chloro-3-indolyl phosphate (BCIP), 6-chloro-3-indolyl phosphate, 5-bromo-6-chloro-3-indolyl phosphate, p-nitrophenyl phosphate, or o-nitrophenyl phosphate or with a fluorogenic substrate such as 4-methylumbelliferyl phosphate, 6,8-difluoro-7-hydroxy-4-methylcoumarinyl phosphate (DiFMUP) fluorescein diphosphate, 3-O-methylfluorescein phosphate, resorufin phosphate, 9H-(1,3-dichloro-9,9-dimethylacridin-2-one-7-yl) phosphate (DDAO phosphate), or ELF 97, ELF 39 or related phosphates.

Glycosidases, in particular β-galactosidase, β-glucuronidase and β-glucosidase, are additional suitable enzymes. Appropriate colorimetric substrates include, but are not limited to, 5-bromo-4-chloro-3-indolyl β-D-galactopyranoside (X-gal) and similar indolyl galactosides, glucosides, and glucuronides, o-nitrophenyl β-D-galactopyranoside (ONPG) and p-nitrophenyl β-D-galactopyranoside. Preferred fluorogenic substrates include resorufin β-D-galactopyranoside, fluorescein digalactoside (FDG), fluorescein diglucuronide and their structural variants, 4-methylumbelliferyl β-D-galactopyranoside, carboxyumbelliferyl β-D-galactopyranoside and fluorinated coumarin β-D-galactopyranosides.

Additional enzymes include, but are not limited to, hydrolases such as cholinesterases and peptidases, oxidases such as glucose oxidase and cytochrome oxidases, and reductases for which suitable substrates are known.

Enzymes and their appropriate substrates that produce chemiluminescence are preferred for some assays. These include, but are not limited to, natural and recombinant forms of luciferases and aequorins. Chemiluminescence-producing substrates for phosphatases, glycosidases and oxidases such as those containing stable dioxetanes, luminol, isoluminol and acridinium esters are additionally useful. For example, the enzyme is luciferase or aequorin. The substrates are luciferine, ATP, $Ca^{++}$ and coelenterazine.

In addition to enzymes, haptens such as biotin are useful detectable moieties. Biotin is useful because it can function in an enzyme system to further amplify a detectable signal, and it can function as a tag to be used in affinity chromatography for isolation purposes. For detection purposes, an enzyme conjugate that has affinity for biotin is used, such as avidin-fluorophore.

Haptens also include hormones, naturally occurring and synthetic drugs, pollutants, allergens, affector molecules, growth factors, chemokines, cytokines, lymphokines, amino acids, peptides, chemical intermediates, or nucleotides.

In some cases, a detectable moiety is a fluorescent protein. Exemplary fluorescent proteins include green fluorescent protein (GFP), the phycobiliproteins and the derivatives thereof, luciferase or aequorin. The fluorescent proteins, especially phycobiliprotein, are particularly useful for creating tandem dye labeled labeling reagents. These tandem dyes comprise a fluorescent protein and a fluorophore for the purposes of obtaining a larger stokes shift where the emission spectra is farther shifted from the wavelength of the fluorescent protein's absorption spectra. This is particularly advantageous for detecting a low quantity of a target in a sample or tissue section where the emitted fluorescent light is maximally optimized, in other words little to none of the emitted light is reabsorbed by the fluorescent protein. For this to work, the fluorescent protein and fluorophore function as an energy transfer pair where the fluorescent protein emits at the wavelength that the fluorophore absorbs at and the fluorphore then emits at a wavelength farther from the fluorescent proteins than could have been obtained with only the fluorescent protein. A particularly useful combination is phycobiliproteins and sulforhodamine fluorophores, or the sulfonated cyanine fluorophores; or the sulfonated xanthene derivatives. Alternatively, the fluorophore functions as the energy donor and the fluorescent protein is the energy acceptor.

Methods of Visualizing a Detection Moiety Depend on the Label.

In some cases, the sample is illuminated with a light wavelength selected to give a detectable optical response, and observed with means for detecting the optical response. Equipment that is useful for illuminating fluorescent compounds described herein includes, but is not limited to, hand-held ultraviolet lamps, mercury arc lamps, xenon lamps, lasers and laser diodes. These illumination sources are optically integrated into laser scanners, fluorescent microplate readers or standard or microfluorometers. The degree and/or location of signal, compared with a standard or expected response, indicates whether and to what degree the sample possesses a given characteristic or desired target.

The optical response is optionally detected by visual inspection, or by use of the following devices: CCD camera, video camera, photographic film, laser-scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, examination of the sample optionally includes sorting portions of the sample according to their fluorescence response.

When an indirectly detectable label is used then the step of illuminating typically includes the addition of a reagent that facilitates a detectable signal such as colorimetric enzyme substrate. Radioisotopes are also considered indirectly detectable wherein an additional reagent is not required but instead the radioisotope must be exposed to X-ray film or some other mechanism for recording and measuring the radioisotope signal. This can also be true for some chemiluminescent signals that are best observed after exposure to film.

As used herein, "specificity" refers to the ability of an antibody to discriminate between antigenic determinants. It also refers to the determinants recognized by a particular receptor or antibody. It also refers to the ability of a receptor to discriminate between substrates, such as drugs. With respect to nucleic acids, it refers to identity or complementarity as a function of competition or recognition/binding, respectively. "Specificity" of recognition or binding may be affected by the conditions under which the recognition or binding takes place (e.g., pH, temperature, salt concentration, and other factors known in the art).

An "effective amount" is an amount sufficient to affect beneficial or desired results. An effective amount may be administered one or more times to achieve the beneficial or desired result.

As used in the specification and claims, the singular forms "a," "an," and "the" include plural references unless the context dictates otherwise. For example, the term "a molecule" can also include a plurality of molecules.

When not otherwise stated, "substantially" means "being largely, but not wholly, that which is specified." The term "about" or "approximately" means within an acceptable error range for the particular value as determined by one of ordinary skill in the art, which will depend in part on how the value is measured or determined, i.e., limitations of the measurement system. For example, "about" can mean within 1 or more than 1 standard deviations, per practice in the art. Alternatively, when referring to a measurable value such as an amount, a temporal duration, a concentration, and the like, may encompass variations of ±20% or ±10%, more preferably ±5%, even more preferably ±1%, and still more preferably ±0.1% from the specified value, as such variations are appropriate to perform the disclosed methods.

EXAMPLES

Materials and Methods
Deparaffinization and Antigen Retrieval:
Tissue slides were deparaffinized by washing various proportions of xylenes and ethanol by following these steps in the following sequence: 1) washed with 100% Xylenes twice, 3 minutes each at room temperature, 2) washed with 1:1 100% Xylenes:100% Ethanol for 3 minutes at room temperature, 3) washed with 100% Ethanol twice, 3 minutes each at room temperature, 4) washed with 95% Ethanol for 3 minutes at room temperature, 5) washed with 70% Ethanol for 3 minutes at room temperature, 6) washed with 50% Ethanol for 3 minutes at room temperature, 7) washed with cold-nuclease free water for 3 minutes at room temperature and then proceed to antigen retrieval procedure. For antigen retrieval, tissue slides were incubated at 80-95° C. in citrate buffer (10 mM Citric Acid, 0.05% Tween 20, pH 6.0) for 30 minutes. However, tissue slides that have frozen tissue sections were subjected to straight antigen retrieval without deparaffinization.

Antibody Staining, Polymerization and Digestion:
Tissue slides were washed with MAXwash™ Washing Medium (Active Motif) and blocked with MAXblock™ Blocking Medium (Active Motif) for up to 3 hours at room temperature (RT) or overnight at 4° C. Tissue slides were incubated with respective primary and secondary antibodies in MAXbind™ Staining Medium (Active Motif) for 6 hours at RT or overnight at 4° C. Upon multiple washes with MAXwash™ Washing Medium (Active Motif) after each antibody incubation, tissue slides were washed with MOPs buffer for 30 minutes, then incubated in a solution of anchoring reagents Acryloyl-X (6-((acryloyl)amino) hexanoic acid succinimidyl ester; 100 m/mL) and NucliX (see below; 100 m/mL) in MOPs buffer for 6 hours or overnight at RT. Anchoring reagent solution was removed and slices were washed with 1×PBS three times. A polymerization solution was prepared by mixing monomer solution, initiator (10% APS) and accelerator (10% TMED) reagents on a vortex. Then polymerization solution was added to the tissue on the slide, gently placed a coverslip and incubated at room temperature for 2 hours. Once the polymerization completed tissue slide with gel was cut to an appropriate size that can fit into a well of 6 well plate and transferred into a Bind-Silane treated glass bottom 6 well plate and subjected to digestion with Proteinase K in digestion buffer for 5 hours at 60° C. then for overnight at room temperature.

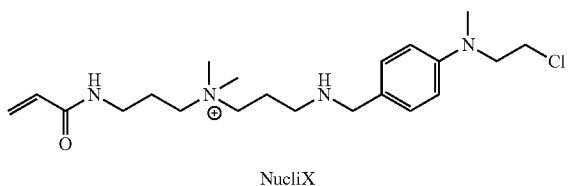 [SMILES: C=CC(=O)NCCC[N+](C)(C)CCCNCc1ccc(N(C)CCCl)cc1]

NucliX

Gel Detachment from the Slide and Expansion:
Digestion buffer was removed, tissue slide with gel was washed with 1×PBS and transferred into a new container. Then tissue slide with gel was heated sequentially 15 minutes in toluene at 60° C., then 5 minutes in water at 60° C. At this point gel will be completed and detached from the slide. The gel was washed with 2×PBS (15 minutes), transferred back into a well of the bind silate treated glass bottom 6 well plate and expanded by washing with cell culture grade water for 4 times 30 minutes each.

Gel Embedding in Polyacrylamide Gel Matrix:
Prepare embedding solution by mixing 3% acrylamide, 0.15% N,N'-Methylenebisacrylamide in 5 mM Tris or Borate buffer and adjust to pH 10.5. Then add the embedding solution, 10% APS and 10% TMED to the expanded gel and incubate on a rocker for 15 minutes. Remove the embedding solution and repeat one more times. Then remove the embedding solution and place an appropriately cut glass slide on top of the gel and incubate at 37° C. for 2 hours.

Restaining with Antibodies:

After embedding, the gel was restained with the respective primary and secondary antibodies in 1×PBS for 6 hours at RT or overnight at 4° C., then subjected to multiple washes with 1×PBS.

Multiplexed In Situ Hybridization:

Re-embedded gel was incubated in wash buffer for 30 minutes at room temperature. Wash buffer was removed and 1 nM of initiator probe (Though 'n' number of initiator probes can be used, we have used 3 probes per hybridization cycle) solution prepared in hybridization buffer was added and the gel was incubated at 37° C. for at least 18 hours. Hybridization buffer with initiator probe was removed and gel was washed wash buffer twice (60 minutes each at 37° C.). Wash buffer was removed and gel was washed with 1×PBS for 2 hours at 37° C. and PBS wash was repeated at room temperature instead of 37° C. 1×PBS was removed and gel was incubated with amplification buffer for 30 minutes at room temperature for pre-amplification. To prepare fluorescently labeled hairpin solution, each HCR hairpin was subjected to snap cooling procedure. In snap cooling procedure each hairpin was heated at 95° C. for 90 seconds, and cooled to room temperature on the benchtop for 30 minutes. Then hairpin solution (60 nM) was prepared by adding all snap-cooled hairpins to amplification buffer at room temperature. Amplification buffer was removed and fresh prepared hairpin solution was added to the gel and incubated for 2-4 hours at room temperature. To stop amplification hairpin solution was removed and gel was washed with 5×SSCT buffer 4 times with 30 minutes incubation each time. Gels were stained with DAPI (100 ng/μL) in water for 15 minutes. Gel is ready to image at this point, Andor Revolution Spinning Disk Confocal microscope was used for imaging. Gels were stored in 0.05×SSC buffer 4° C.

Probe Removal by DNAse I Digestion:

To remove the probes and prepare the gel/specimen for next round of in situ hybridization with next set of probes, 0.05×SSC buffer was removed and gels were incubated with 0.25 U/μL of DNAse I in Reaction Buffer for at least 6 hours to overnight at 37° C. DNAse I was removed and the gel was washed with 1×PBS and stored in 1×PBS at 4° C. until imaging. Images were collected using Andor Revolution Spinning Disk Confocal microscope, then gel/specimen was proceeded with next round of in situ hybridization of next set of probes.

Bind-Silane Treatment:

Prepare Bind-Silane solution by mixing 5 μL of Bind-Silane, 8 mL of ethanol, 1.8 mL of nuclease free water and 0.2 mL of acetic acid in a falcon tube. Then add 1 mL Bind-silane solution to each well of glass bottom 6 well plate and incubate for 10 minutes at room temperature. Remove Bind-silane solution and let air dry for 10 minutes, wash twice with EtOH and let air dry for 30-60 minutes.

Storing the Tissue:

Fresh frozen and FFPE tissue sections on frosted glass slide were purchased from various commercial sources (USBiomax, Biochain, Analytical Biological Services, Zyagen etc.). These sections were prepared in RNAse free conditions and stored at recommended temperature (−80° C. or room temperature).

Example 1

Figure 1B:
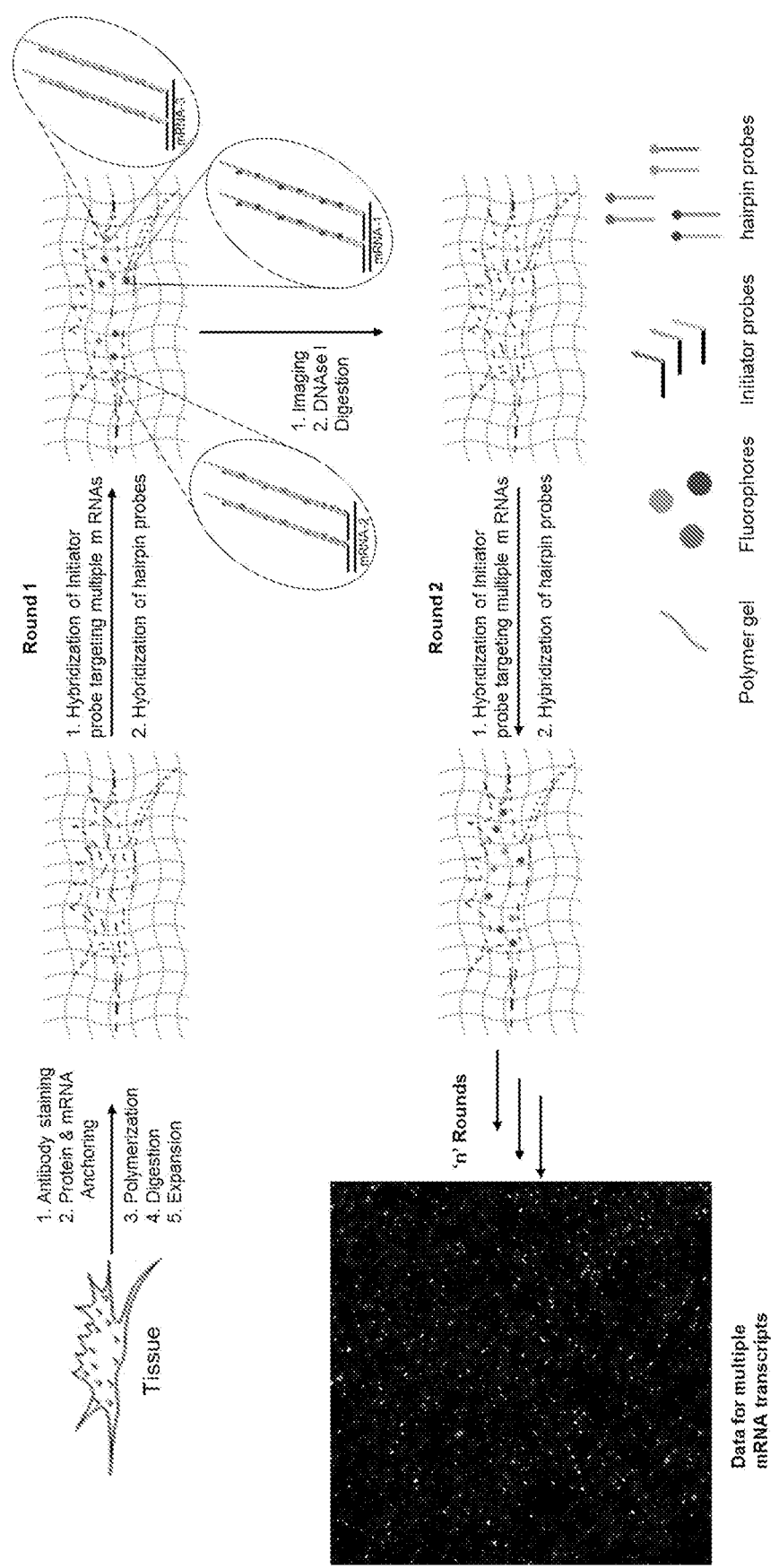

As shown in FIGS. 1A and 1B, and an FFPE biological sample adhered on a slide (e.g., a frosted glass slide) is obtained. Under RNAse-free conditions, the sample undergoes deparaffinization, followed by antigen retrieval and subsequent staining with primary and secondary antibodies. Also under RNAse-free conditions, the RNA in the sample is linked, directly or indirectly, to a gel binding moiety. The sample is then contacted with a solution comprising monomers of a polyelectrolyte gel, which are then polymerized by free radical polymerization to form the polyelectrolyte gel, as well as anchoring the protein and RNA to the gel. The sample is digested, and the gel is detached from the slide; the gel is then dialyzed to expand it, optionally followed by polyacrylamide embedding and imaging. The next step is probe hybridization, HCR amplification, followed by washing, imaging, and digestion with DNAse I. Subsequent rounds of probe, hybridization, HCR amplification, washing, imaging, and DNAse digestion are conducted.

Example 2

More specifically, for an RNA target of interest (e.g., an mRNA), a single-stranded DNA probe is provided having a 5' sequence complementary or partially complementary to a sequence of the RNA target of interest, and a 3' HCR initiator domain having a first initiator segment and a 3' second initiator segment. The probe is optionally also operably linked to a detectable label. The expanded gel is contacted with the DNA probe under conditions to selectively hybridize with the RNA target of interest. If the probe includes a detectable label, an image may be taken of the gel.

An HCR amplifier is provided, which comprises a first DNA hairpin molecule and a second DNA hairpin molecule, and which coexist metastably in the absence of the probes hybridized to the RNA target of interest. The first DNA hairpin molecule sequentially comprises (i) a first domain comprising a 5' tail complementary or partially complementary to the 3' second initiator segment of the 3' HCR intiator domain of the probe, (ii) a second domain complementary or partially complementary to the first initiator segment of the 3' HCR initiator domain of the probe, (iii) a third domain, and (iv) a fourth domain complementary or partially complementary to the first domain. The second DNA hairpin molecule sequentially comprises (i) a first domain comprising a 5' domain complementary or partially complementary to the second domain of said first DNA hairpin molecule, (ii) a second domain complementary or partially complementary to the first domain of said first DNA hairpin molecule, (iii) a third domain complementary or partially complementary to the first domain of the second DNA hairpin molecule, and (iv) a fourth domain comprising a 3' tail complementary or partially complementary to the third domain of the first DNA hairpin molecule. One or both of the first or second DNA hairpin molecules is operably linked to a detectable label, such as a fluorophore.

The gel is contacted with the HCR amplifier (first and second DNA hairpin molecules) under conditions in which (a) the 3' second initiator segment of the 3' HCR initiator domain of the probe selectively hybridizes to the first domain of said first DNA hairpin molecule, initiating a hybridization chain reaction, (b) the second domain of the first DNA hairpin molecule hybridizes to the first initiator segment of the 3' HCR initiator domain of the probe, exposing the third domain of the first DNA hairpin molecule, and (c) the third domain of the first DNA hairpin molecule hybridizes to the fourth domain of the second DNA hairpin molecule exposing the second domain of the second DNA hairpin molecule and the first domain of the second DNA hairpin molecule.

Additional first and second DNA hairpin molecules are hybridized, resulting in a series of extensions, each with at least one additional detectable label (two if both the first and second DNA hairpin molecules comprise detectable label(s)).

The detectable label is detected, and the results are imaged. Optionally, the gel is treated with DNAse I, and subsequent rounds of hybridization, washing, imaging, and DNAse digestion are conducted.

Example 3

For an RNA target of interest (e.g., an mRNA) in a biological sample of interest, and a plurality of unique single-stranded DNA probes are provided. Each unique probe has a 5' sequence complementary or partially complementary to a unique sequence of mRNA target of interest, and a 3' HCR initiator domain having a first initiator segment and a 3' second initiator segment The probes are optionally also operably linked to a detectable label. The expanded sample is contacted with the DNA probes under conditions to selectively hybridize with the RNA targets of interest. If the probes include a detectable label, an image may be taken of the gel.

An HCR amplifier is provided. The HCR amplifier comprises a first DNA hairpin molecule and a second DNA hairpin molecule, which coexist metastably in the absence of the probes hybridized to the RNA target of interest. The first DNA hairpin molecule sequentially comprises (i) a first domain comprising a 5' tail complementary or partially complementary to the 3' second initiator segment of the 3' HCR initiator domain of the probes, (ii) a second domain complementary or partially complementary to the first initiator segment of the 3' HCR initiator domain of the probes, (iii) a third domain, and (iv) a fourth domain complementary or partially complementary to the first domain. The second DNA hairpin molecule sequentially comprises (i) a first domain comprising a 5' domain complementary or partially complementary to the second domain of said first DNA hairpin molecule, (ii) a second domain complementary or partially complementary to the first domain of said first DNA hairpin molecule, (iii) a third domain complementary or partially complementary to the first domain of the second DNA hairpin molecule, and (iv) a fourth domain comprising a 3' tail complementary or partially complementary to the third domain of the first DNA hairpin molecule. One or both of the first or second DNA hairpin molecules is operably linked to a detectable label.

The gel is contacted with the HCR amplifier (first and second DNA hairpin molecules) under conditions in which (a) the 3' second initiator segment of the 3' HCR initiator domain of each of the probes selectively hybridizes to a first domain of a first DNA hairpin molecule, initiating a hybridization chain reaction, (b) the second domain of the first DNA hairpin molecule hybridizes to the first initiator segment of the 3' HCR initiator domain of the probes, exposing the third domain of the first DNA hairpin molecule, and (c) wherein the third domain of the first DNA hairpin molecule hybridizes to the fourth domain of the second DNA hairpin molecule exposing the second domain of the second DNA hairpin molecule and the first domain of the second DNA hairpin molecule.

Additional first and second DNA hairpin molecules are hybridized, resulting in a series of extensions, each with at least one additional detectable label (two if both the first and second DNA hairpin molecules comprise detectable label(s)).

The detectable label is detected, and the results are imaged. Optionally, the gel is treated with DNAse I, and subsequent rounds of hybridization, washing, imaging, and DNAse digestion are conducted.

Example 4

For a plurality of RNA targets of interest (e.g., a plurality of mRNAs) in a FFPE biological sample of interest, A plurality of unique single-stranded DNA provided are provided. Each unique DNA probe has a 5' sequence complementary or partially complementary to a unique domain sequence of one of the RNA targets of interest, and a 3' HCR initiator domain having a first initiator segment and a 3' second initiator segment. The probe is optionally also operably linked to a detectable label. The expanded gel is contacted with the DNA probes under conditions to selectively hybridize with the RNA targets of interest. If the probe includes a detectable label, an image may be taken of the gel.

A plurality of unique HCR amplifiers is provided. Each unique HCR amplifier corresponds to a unique probe and comprises a unique first DNA hairpin molecule and a unique second DNA hairpin molecule, which coexist metastably in the absence of the probes hybridized to the RNA targets of interest. Each unique first DNA hairpin molecule sequentially comprises (i) a first domain comprising a 5' tail complementary or partially complementary to the 3' second initiator segment of the 3' HCR initiator domain of the corresponding probe, (ii) a second domain complementary or partially complementary to the first initiator segment of the 3' HCR initiator domain of that probe, (iii) a third domain, and (iv) a fourth domain complementary or partially complementary to the first domain. The second DNA hairpin molecule sequentially comprises (i) a first domain comprising a 5' domain complementary or partially complementary to the second domain of said first DNA hairpin molecule, (ii) a second domain complementary or partially complementary to the first domain of said first DNA hairpin molecule, (iii) a third domain complementary or partially complementary to the first domain of the second DNA hairpin molecule, and (iv) a fourth domain comprising a 3' tail complementary or partially complementary to the third domain of the first DNA hairpin molecule. One or both of the unique first or second DNA hairpin molecules is operably linked to a unique detectable label.

The gel is contacted with the plurality of HCR amplifiers (unique first and second DNA hairpin molecules) under conditions in which, with respect to each unique first and second nucleic acid hairpin molecules of each unique HCR amplifier, (a) the 3' second initiator segment of the 3' HCR initiator domain of each of the corresponding probes selectively hybridizes to a first domain of a first DNA hairpin molecule, initiating a hybridization chain reaction, (b) the second domain of the first DNA hairpin molecule hybridizes to the first initiator segment of the 3' HCR initiator domain of the probe, exposing the third domain of the first DNA hairpin molecule, and (c) wherein the third domain of the first DNA hairpin molecule hybridizes to the fourth domain of the second DNA hairpin molecule exposing the second domain of the second DNA hairpin molecule and the first domain of the second DNA hairpin molecule.

Additional unique first and second DNA hairpin molecules are hybridized, resulting in a series of extensions, each with at least one additional detectable label (two if both the first and second DNA hairpin molecules comprise detectable label(s)).

Each unique detectable label is detected, and the results are imaged. Optionally, the gel is treated with DNAse I, and subsequent rounds of hybridization, washing, imaging, and DNAse digestion are conducted.

Example 5

Figure 2:
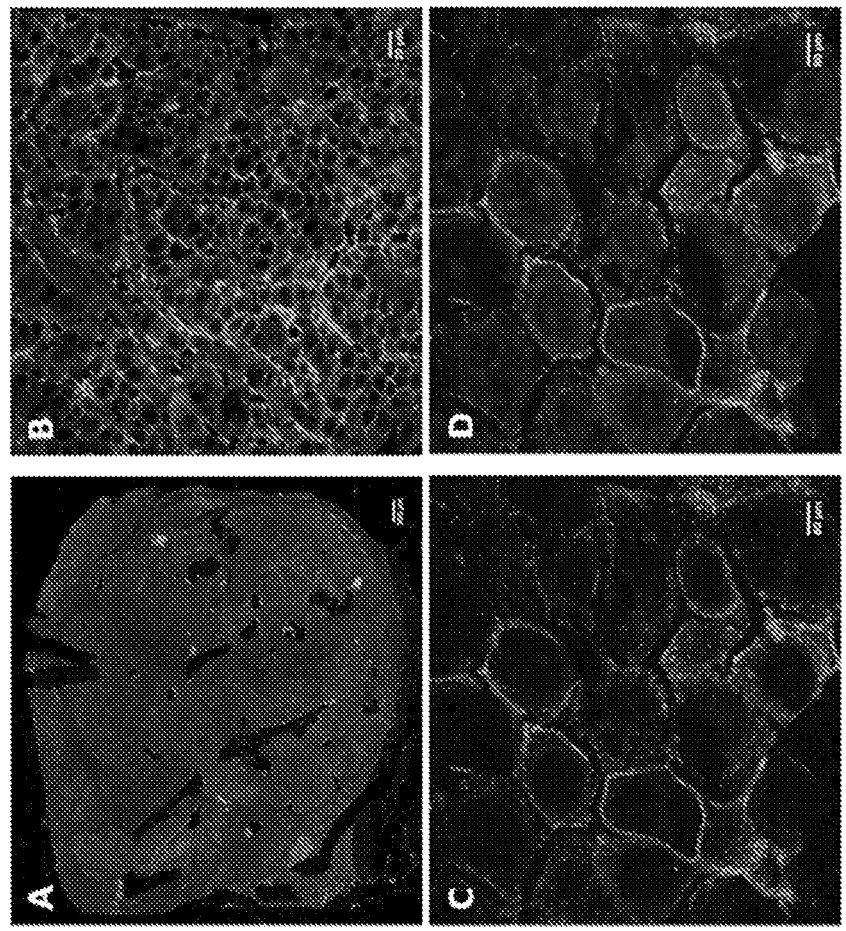
FIGS. 2A-2D. Pre-expansion and post-expansion photographs showing images of a breast cancer FFPE tissue section stained with anti-Her2 antibody. The breast cancer shown is an invasive duct carcinoma of the right breast. The photographic images show the following: (A) whole tissue section on the slide (pre-expansion); (B) enlarged detail of a portion of the sample in FIG. 2A; (C) portion of the post-expansion image without staining by 4',6-diamidino-2-phenylindole (without DAPI stain); and (D) post-expansion image of the same section as (C) with DAPI stain.

As shown in FIGS. 2A-2D, an FFPE tissue section of an invasive duct carcinoma of the right breast underwent deparaffinization and antigen retrieval. The tissue section was then stained with anti-Her2 antibody and photographed. FIG. 2A shows the stained, whole tissue section on the slide prior to expansion, with FIG. 2B showing an enlarged detail of a portion of the sample shown in FIG. 2A. After expansion, the tissue section was photographed again, stained with 4',6-diamidino-2-phenylindole (DAPI), and then re-photographed. FIG. 2C shows a post-expansion image of a portion of the tissue section after expansion, but prior to staining with DAPI, while FIG. 2D shows a post-expansion image of the same section as FIG. 2C following DAPI staining.

Example 6

Figure 3:
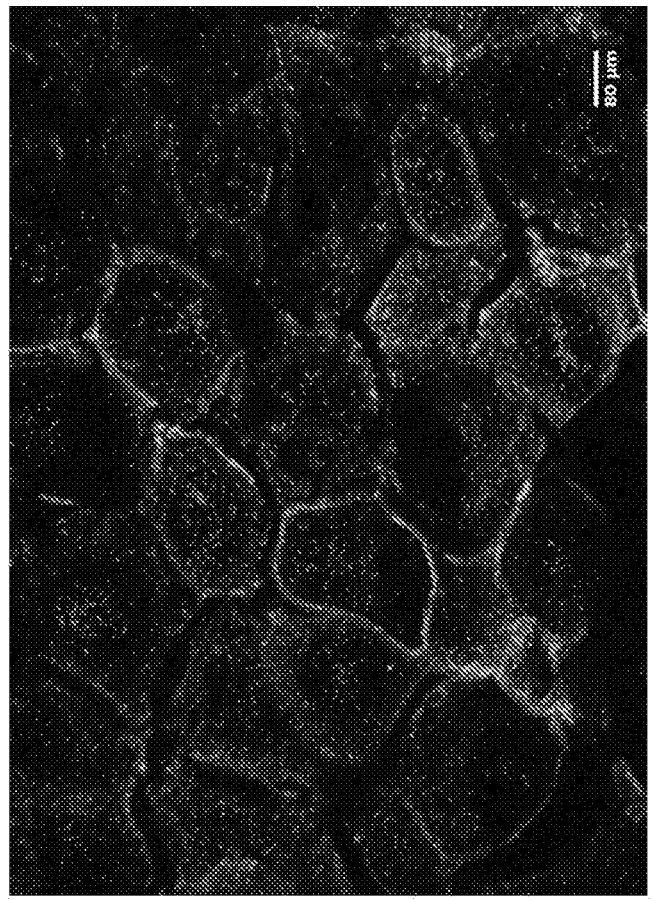
FIG. 3. Photograph of the portion of the section in FIGS. 2C-2D of invasive duct carcinoma of the right breast. The image was taken after RNA Fluorescence In Situ Hybridization (FISH) of ERBB2 (Her2) mRNA of the breast cancer FFPE tissue section.

FIG. 3 shows further screening of the same portion of the tissue section in FIGS. 2C-2D of the invasive duct carcinoma of the right breast following RNA Fluorescence In Situ Hybridization (FISH) of ERBB2 mRNA of the breast cancer FFPE tissue section and Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A method of labeling nucleic acids and proteins together in a formalin fixed paraffin embedded (FFPE) biological sample adhered on a glass slide, said method being performed under RNAse-free conditions and said method comprising:
   (a) performing deparaffinization and antigen retrieval on the sample;
   (b) contacting the sample with a first gel binding moiety and a second gel binding moiety under conditions wherein the first gel binding moiety operably links to proteins in the sample and the second gel binding moiety operably links to nucleic acids in the sample and comprises

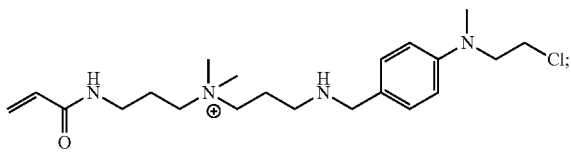 [SMILES: C=CC(=O)NCCC[N+](C)(C)CCCNCc1ccc(N(C)CCCl)cc1]

(c) contacting the sample with a solution comprising monomers of a polyelectrolyte gel;
   (d) by free radical polymerization, polymerizing said monomers to form the polyelectrolyte gel and covalently conjugating the first and second gel binding moieties to the polyelectrolyte gel;
   (e) proteolytically digesting said sample;
   (f) detaching the gel from the slide;
   (g) dialyzing the polyelectrolyte gel to expand it;
   (h) providing a plurality of initiator deoxyribonucleic acid (DNA) probes targeting a plurality of nucleic acid targets of interest, wherein each of the plurality of initiator DNA probes comprise (A) a sequence complementary to a sequence from one of the nucleic acid targets of interest, and (B) a hybridization chain reaction (HCR) initiator sequence;
   (i) contacting the gel with the plurality of initiator DNA probes under conditions wherein the sequence complementary to the sequence from one of the nucleic acid targets of interest hybridizes to that sequence from the nucleic acid target of interest;
   (j) for each initiator DNA probe, providing a pair of fluorophore-labeled DNA hairpins that metastably co-exist in the absence of the initiator DNA probe; and
   (k) contacting the gel with the fluorophore-labeled DNA hairpins under conditions wherein the hairpins self-assemble by HCR, in the presence of their corresponding initiator DNA probe, into fluorescent amplification polymers tethered to that corresponding initiator DNA probe.

2. The method of claim 1, further comprising the step of washing the gel to remove unhybridized initiator DNA probes and fluorophore-labeled DNA hairpins that have not been incorporated into fluorescent amplification polymers.

3. The method of claim 1, further comprising, prior to step (h), embedding the expanded gel in a polyacrylamide gel matrix.

4. The method of claim 3, wherein the expanded gel is embedded in the polyacrylamide gel matrix in a borate buffer.

5. The method of claim 1, wherein the plurality of nucleic acid targets of interest comprise mRNA.

6. The method of claim 1, wherein the first and/or second gel binding moiety has an acryloyl or a methacryloyl group.

7. The method of claim 6, wherein the first gel binding moiety is Acryloyl-X (6-((acryloyl)amino)hexanoic acid succinimidyl ester).

8. The method of claim 1, further comprising, prior to step (b):
   (I) contacting the sample with one or more primary antibodies under conditions where they selectively recognize one or more target proteins of interest; and
   (II) contacting the sample with one or more secondary antibodies operably linked to a detectable label.

9. The method of claim 8, wherein the steps of (I) contacting the sample with one or more primary antibodies under conditions where they selectively recognize one or more target proteins of interest; and (II) contacting the sample with one or more secondary antibodies operably linked to a detectable label; are repeated after the gel is detached from the slide.

10. The method according to claim 1, wherein said monomer solution comprises sodium acrylate, acrylamide, N-N'-methylenebisacrylamide, and N,N-dimethyl-acrylamide.

11. The method according to claim 1, wherein said free radical polymerization is induced with ammonium persulfate (APS) initiator and tetramethylethylenediamine (TEMED).

12. The method according to claim 1, wherein dialyzing the polyelectrolyte gel to expand it comprises dialyzing said gel in water to expand said polyelectrolyte gel.

13. The method according to claim 1, wherein antigen retrieval comprises heat-induced epitope retrieval (HIER).

14. The method according to claim 13, wherein HIER comprises incubation of the sample in a buffer comprising a citrate buffer, a 2-amino-2-(hydroxymethyl)propane-1,3-diol (Tris) buffer, an ethylenediaminetetraacetic acid (EDTA) buffer, a Tris-EDTA buffer, a citrate-EDTA buffer, or Tris-buffered saline (TBS).

15. The method according to claim 1, wherein antigen retrieval comprises proteolytic-induced epitope retrieval (PIER) or enzyme-induced antigen retrieval (EIAR), room temperature epitope retrieval (RTER), frozen section epitope retrieval, retrieval with sodium citrate and milk, or retrieval with citraconic anhydride.

16. The method according to claim 1, where detaching the gel from the slide comprises heating the slide with the gel sequentially in toluene and then in water.

17. The method according to claim 1, wherein the biological sample has been stained with hematoxylin and eosin (H&E).

18. A method of imaging nucleic acids and proteins together in a formalin fixed paraffin embedded (FFPE) biological sample adhered on a glass slide, said method being performed under RNAse-free conditions and said method comprising the method of claim 1 and obtaining an image of the gel.

19. A method of imaging nucleic acids and proteins together in a formalin fixed paraffin embedded (FFPE) biological sample adhered on a glass slide, said method being performed under RNAse-free conditions and said method comprising carrying out the steps of claim 1, and
   (l) obtaining an image of the gel;
   (m) treating the gel with a deoxyribonuclease to remove the initiator DNA probes and amplification polymers; and repeating steps (h)-(m) one or more times for additional nucleic acid targets of interest.

* * * * *